US006448245B1

(12) United States Patent
DePetrillo et al.

(10) Patent No.: US 6,448,245 B1
(45) Date of Patent: Sep. 10, 2002

(54) METHODS OF AND COMPOUNDS FOR INHIBITING CALPAINS

(75) Inventors: Paolo B. DePetrillo, Bethesda; Wenshuai Wan, Ellicott City, both of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/847,872

(22) Filed: May 2, 2001

Related U.S. Application Data

(60) Provisional application No. 60/202,378, filed on May 4, 2000.

(51) Int. Cl.[7] .................. A61K 31/55; A61K 31/495; A61K 31/47; A61K 31/425; A61K 31/34
(52) U.S. Cl. ............... 514/218; 514/252.13; 514/311; 514/365; 514/461
(58) Field of Search .................. 514/218, 252.13, 514/311, 365, 461

(56) References Cited

U.S. PATENT DOCUMENTS

| | | |
|---|---|---|
| 5,196,438 A | 3/1993 | Martin et al. |
| 5,413,999 A | 5/1995 | Vacca et al. |
| 5,424,426 A | 6/1995 | Häbich et al. |
| 5,484,926 A | 1/1996 | Dressman et al. |
| 5,541,206 A | 7/1996 | Kempf et al. |

FOREIGN PATENT DOCUMENTS

| | | |
|---|---|---|
| EP | 0 720 987 A1 | 7/1996 |
| EP | WO 98/56781 | 12/1998 |
| EP | 0 955 054 A1 | 11/1999 |
| WO | WO 98/22106 | 5/1998 |

OTHER PUBLICATIONS

Wang, Kevin K.W., and Yuen, Po–Wai, Development and Therapeutic Potential of Calpain Inhibitors, Advances in Pharmacology, 37:117–51 (1997).
Robinson, Alex, Inhibiting Calpain, Rescuing Cells, Can. Med. Assoc. J., 154(2):193–95 (1996).
Arthur, J. Simon C., and Elce, John S., Interaction of Aspartic Acid–104 and Proline–287 with the Active Site of M–Calpain, Biochemical J., 319:535–41 (1996).
Goldgur, Yehuda, et al., Structure of the HIV–1 Integrase Catalytic Domain Complexed with an Inhibitor; A platform for Antiviral Drug Design, Proc. Nat'l Acad. Sci. USA, 96(23):13040–43 (1999).
Debnath, Asim Kumar, Three–Dimensional Quantitive Structure–Activity Relationship Study on Cyclic Urea Derivative as HIV–1 Protease Inhibitors: Application of Comparative Molecular Field Analysis, J. Med. Chem., 42(2):249–59 (1999).
Chatterjee, et al., Synthesis and Biological Activity of a Series of Potent Fluoromethyl Ketone Inhibitors of Recombinant Human Calpain I, J. Med. Chem., 40(23):3820–28 (1997).

Wang, Kevin K.W., and Yuen, Po–Wai, Calpain Inhibition: An Overview of its Therapeutic Potential, TiPS, 15:412–19 (1994).
Strobl, Stefan, et al., The Crystal Structure of Calcium–Free Human M–Calpain Suggest an Electrostatic Switch Mechanism for Activation by Calcium, Proc. Natl Acad. Sci. USA, 97(2):588–92 (2000).
Hosfield, Christopher M., et al., Crystal Structure of Calpain Reveals the Structural Basis for $Ca^{2+}$–Dependent Protease Activity and a Novel Mode of Enzyme Activity, The EMBO Journal, 18(24):6880–89 (1999).
Eriksson, U., et al, Is Treatment with Ritonavir a Risk Factor for Myocardial Infarction in HIV–Infected Patients?, AIDS, 12(15):2079–80 (1998).
Flynn Thomas E., and Bricker Lee A., Myocardial Infarction in HIV–Infected Men Receiving Protease Inhibitors, Annals of Internal Medicine, 131(7):548 (1999).
Sorimachi, Hiroyuki, et al., New Era of Calpain Research: Discovery of Tissue–Specific Calpains, FEBS Letters 343:1–5 (1994).
Sorimachi, Hiroyuki, et al., Structure and Physiological Function of Calpains, Biochem. J. 328:721–32 (1997).
Behrens, Georg, et al., Vascular Complications Associated with use of HIV Protease Inhibitors, The Lancet, 351:1958 (1998).
Gallet, Bruno, et al., Vascular Complications Associated with use of HIV Protease Inhibitors, The Lancet, 351:1958–59 (1998).
Vittecog, D. et al., Vascular Complications Associated with use of HIV Protease Inhibitors, The Lancet, 351:1959 (1998).
Laurence, Jeffrey, Vascular Complications Associated with use of HIV Protease Inhibitors, The Lancet, 351:1960 (1998).
Arthur, J. Simon C., et al., Active Site Residues in M–Calpain: Identification by Site–Directed Mutagenesis, FEBS Letters, 368:397–400 (1995).
Wang, Kevin K. W., et al., An Alpha–Mercaptoacrylic Acid Derivative is a Selective Nonpeptide Cell–Permeable Calpain Inhibitor and is Neuroprotective, Proc. Natl. Acad. Sci. USA, 93:6687–92 (1996).

*Primary Examiner*—Raymond Henley, III
(74) *Attorney, Agent, or Firm*—Klarquist Sparkman, LLP

(57) ABSTRACT

A method is disclosed for inhibiting calpain by contacting calpain with one or more HIV protease inhibitors or analogs. Included are embodiments for identifying subjects at risk of suffering calpain-mediated physiological damage and administering to them the HIV protease inhibitors or analogs. Alternatively, a compound may be administered to a subject following an actual event implicating activation of calpain. Also included are methods of treating or preventing calpain-mediated physiological damage in a subject by administering to the subject a therapeutically effective amount of a pharmaceutical composition which includes at least one HIV protease inhibitor or analog. The pharmaceutical compositions can be used in the treatment of a variety of conditions or diseases implicated by or associated with calpain activation, including cardiovascular diseases.

48 Claims, No Drawings

METHODS OF AND COMPOUNDS FOR INHIBITING CALPAINS

CROSS-REFERENCE TO RELATED APPLICATION

This application claims the benefit of U.S. Provisional application No. 60/202,378, filed on May 4, 2000, herein incorporated by reference.

FIELD

This invention relates to enzymatic inhibitors, particularly calpain inhibitors, and more particularly, calpain inhibition by HIV protease inhibitors.

BACKGROUND

Calpains and Calpain Inhibitors

Calpains are mammalian calcium-dependent neutral cysteine proteases involved in programmed cell death (apoptosis). Calpains are referred to as cysteine proteases because they include a cysteine residue that plays a critical role in the catalytic process. In the presence of calcium, a cysteine protease catalytic triad forms when three amino acid residues (Cys 105, His262, and Asn 286) are brought together in the active site.

Two major classes of calpains are known, μ-calpain and m-calpain, which differ in their sensitivities toward calcium. Some tissue-specific forms of calpain also have been identified. Substrates of calpain include cellular proteins such as cytoskeletal proteins, membrane-bound receptors, calmodulin binding proteins, myofibrillar proteins, enzymes, and transcription factors.

Calpain can become activated under ischemic conditions. It has been proposed that ischemia overactivates cellular membrane receptors, which causes an influx of calcium ions into the cell. This influx activates calcium-dependent enzymes, including calpains, and the calpains begin digesting cellular proteins, which contributes to cell death.

Inhibition of calpain has provided therapeutic possibilities for a number of different diseases, including cerebral ischemia (particularly strokes), traumatic brain injury, subarachnoid hemorrhage, chronic neurodegeneration (e.g., Huntington's disease, Parkinson's disease, and amyotrophic lateral sclerosis), Alzheimer's disease, cardiac ischemia (particularly myocardial infarction), muscular dystrophy, cataracts, thrombotic platelet aggregation, restenosis, and joint inflammation (particularly arthritis).

A more detailed overview of calpains and calpain inhibitors can be found in Wang, et al., *Advances in Pharmacology*, 37:117–52 (1997). Patents disclosing calpain inhibitors include: Zimmerman, et al., U.S. Pat. No. 5,374,623; Wang, et al., U.S. Pat. No. 5,760,048; Munoz, et al., U.S. Pat. No. 5,872,101; Munoz, et al., U.S. Pat. No. 5,969,100; and Spruce, et al., U.S. Pat. No. 6,004,933.

HIV Protease and Inhibitors

The human immunodeficiency virus (HIV) is a retrovirus that causes immunosuppression in humans and leads to a disease complex known as acquired immunodeficiency syndrome (AIDS). HIV protease is an aspartyl protease that plays a central role in viral processing by cleaving the HIV GAG and GAG-POL polypeptides to produce mature viral core proteins and virus-specific enzymes. The HIV protease is called an aspartyl protease due to an important aspartyl residue in the active site that hydrolyzes the peptide bond of its substrate. Coffin et al., *Retroviruses* (Cold Spring Harbor Laboratory Press, 1997), provides a more detailed explanation of HIV protease.

Commercially available HIV protease inhibitors include ritonavir, saquinavir, indinavir, nelfinavir, and amprenavir. Numerous other HIV protease inhibitors are currently being tested in humans, but have not yet been approved by the United States Food and Drug Administration (FDA) for use against HIV, including ABT378, BMS232632, DMP450, GW433908, L-756,423, and timpranavir. Other HIV protease inhibitors have been disclosed in the patent literature, including: Martin et al., U.S. Pat. No.5,196,438; Vacca et al., U.S. Pat. No. 5,413,999; Dressman et al., U.S. Pat. No. 5,484,926; Kempf et al., U.S. Pat. No. 5,541,206; WO 97/0139 and WO 00/04016 by Abbott Laboratories; and WO 98/56781 by Glaxo Group Limited.

SUMMARY

A variety of calpain inhibitors are disclosed, as well as methods of using these inhibitors to treat conditions associated with calpain activation. In some embodiments, HIV inhibitors are used to inhibit calpain activity. In other embodiments, the calpain inhibitor is an analog of or compound related to an HIV protease inhibitor.

A calpain may be inhibited by contacting the calpain with a disclosed inhibitor, such as an HIV protease inhibitor, analog, or related compound. In some embodiments, the calpain inhibitor is administered in therapeutically effective amounts to inhibit calpains within cells of subjects. In other embodiments, the calpain inhibitor is a compound having one or more of the following structures or clinical names, without reference to the ability of that compound to inhibit HIV protease activity:

(1) compounds of the formula,

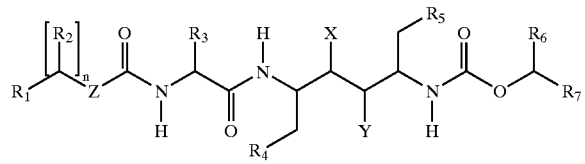

wherein $R_1$ is monosubstituted thiazolyl, monosubstituted oxazolyl, monosubstituted isoxazolyl, or monosubstituted isothiazolyl; and wherein the substituent is selected from: lower alkyl; lower alkenyl; cycloalkyl; cycloalkylalkyl; cycloalkenyl; cycloalkenylalkyl; heterocyclic, wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl, and pyrazinyl and wherein the heterocyclic is unsubstituted or substituted with a substituent selected from halo, lower alkyl, hydroxy, alkoxy, and thioalkoxy; (heterocyclic)alkyl, wherein the heterocyclic is defined as above; alkoxyalkyl; thioalkoxyalkyl; alkylamino; dialkylamino; phenyl, wherein the phenyl ring is unsubstituted or substituted with a substituent selected from halo, lower alkyl, hydroxy, alkoxy and thioalkoxy; phenylalkyl, wherein the phenyl ring is unsubstituted or substituted with a substituent selected from halo, lower alkyl, hydroxy, alkoxy and thioalkoxy; dialkylaminoalkyl; alkoxy; and thioalkoxy;

n is 1, 2 or 3;

$R_2$ is hydrogen or a lower alkyl;

$R_3$ is a lower alkyl;

$R_4$ and $R_5$ are independently selected from phenyl, thiazolyl, and oxazolyl, wherein the phenyl, thiazolyl or oxazolyl ring is unsubstituted or substituted with a substituent selected from halo, lower alkyl, hydroxy, alkoxy, and thioalkoxy;

$R_6$ is hydrogen or lower alkyl;

$R_7$ is thiazolyl, oxazolyl, isoxazolyl or isothiazolyl, wherein the thiazolyl, oxazolyl, isoxazolyl or isothiazolyl ring is unsubstituted or substituted with lower alkyl;

X is hydrogen and Y is —OH, or X is —OH and Y is hydrogen, with the proviso that X is hydrogen and Y is —OH when Z is —N($R_8$)— and $R_7$ is unsubstituted, and with the proviso that X is hydrogen and Y is —OH when $R_3$ is methyl and $R_7$ is unsubstituted; and Z is absent, —O—, —S—, —$CH_2$— or —N($R_8$)— wherein $R_8$ is a lower alkyl, cycloalkyl, —OH or —NH$R_9$, wherein $R_9$ is hydrogen, lower alkyl or an N-protecting group; or (2) compounds of the formula,

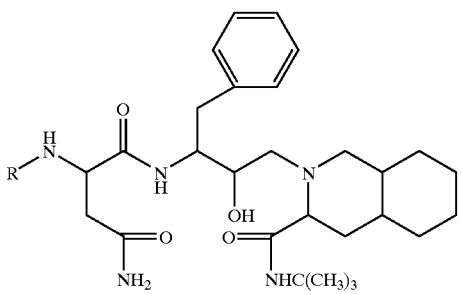

wherein R is benzyloxycarbonyl or 2-quinolylcarbonyl; or, (3) any of: ritonavir; saquinavir; indinavir; nelfinavir; or amprenavir.

Subjects at risk of suffering calpain-mediated physiological damage may be identified and administered an HIV protease inhibitor, or another compound disclosed herein, following an event associated with activation of calpain, such as ischemia in the cardiovascular (including the neurovascular) system, or the myocardial or neural tissues which these systems perfuse.

Some embodiments include treating or preventing calpain-mediated physiological damage in a subject. In these embodiments, calpain-mediated physiological damage is treated by administering to a subject a therapeutically effective amount of a pharmaceutical composition having at least one protease inhibitor. Particular examples of pharmaceutical compositions include those with plural HIV protease inhibitors; pharmaceutically compatible carriers, agents, counterions, adjuvants, or vehicles; and/or other calpain inhibitors (in addition to the compounds disclosed herein). Treatments may be prophylactic or reparative.

Particular examples of therapeutically effective amounts of compounds include amounts that provide an inhibition constant, $K_i$, for inhibition of calpain less than or equal to about 11 μM. Additionally, therapeutically effective doses of compounds may be administered to a subject for a limited period of time, such as about a month, a week, or even less than about 72 hours.

The pharmaceutical compositions can be used to treat a variety of conditions or diseases associated with calpain activation, including cardiovascular diseases. In particular embodiments, the treated condition is ischemia, such as myocardial or neural ischemia, resulting from decreased oxygenation of these tissues, as may occur in myocardial infarction, coronary stenosis or vasospasm, cerebrovascular accidents, such as ischemic or hemorrhagic stroke, and neurological trauma.

DETAILED DESCRIPTION

Explanations of Terms

An "animal" is a living multicellular vertebrate organism, a category which includes, for example, mammals and birds.

The article "a" or "an" includes both the singular or plural, unless the context of its use clearly indicates otherwise.

The term "amino" refers to a chemical functionality —$NR_1R_2$ where $R_1$ and $R_2$ are independently hydrogen, alkyl, or aryl.

The term "activated ester derivative" refers to acid halides, such as acid chlorides, and activated esters including, but not limited to, formic and acetic acid derived anhydrides, anhydrides derived from alkoxycarbonyl halides (such as isobutyloxycarbonylchloride), N-hydroxysuccinimide derived esters, N-hydroxyphthalimide derived esters, N-hydroxybenzotriazole derived esters, N-hydroxy-5-norbomene-2,3-dicarboxamide derived esters, and 2,4,5-trichlorophenol derived esters and the like.

An "analog" is a molecule that is structurally similar to another molecule but which differs slightly in chemical structure from a parent compound, for example by the replacement of one atom by an atom of a different element, or by the substitution of one functional group for another. Examples include, but are not limited to, a homolog (which differs by an increment in the chemical structure, such as a difference in the length of an alkyl chain), a molecular fragment, a structure that differs by one or more functional groups, or a change in ionization. Structural analogs are often found using quantitative structure activity relationships (QSAR), with techniques such as those disclosed in *Remington: The Science and Practice of Pharmacology*, 19th Edition (1995), chapter 28. A derivative is a biologically active molecule derived from the base molecular structure. A mimetic is a biomolecule that mimics the activity of another biologically active molecule. Biologically active molecules can include both chemical structures and peptides that mimic the calpain inhibition activities of the compounds disclosed herein, regardless of whether they also inhibit HIV protease activity.

The term "alkylamino" refers to a lower alkyl radical appended to an —NH radical.

The term "alkoxy" refers to a substituted or unsubstituted alkoxy, where an alkoxy has the structure —O—R, where R is a substituted or unsubstituted alkyl. In an unsubstituted alkoxy, the R is an unsubstituted alkyl. The term "substituted alkoxy" refers to a group having the structure —O—R, where R is alkyl which is substituted with a non-interfering substituent. "Lower alkoxy" refers to any alkoxy in which R is a lower alkyl. "Thioalkoxy" refers to —S—R, where R is substituted or unsubstituted alkyl.

The term "alkoxyalkyl" refers to an alkoxy group appended to a lower alkyl radical.

The term "alkyl" refers to a cyclic, branched, or straight chain alkyl group containing only carbon and hydrogen, which, unless otherwise described, contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can be unsubstituted or substituted with one or more substituents, for example halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "aryl" refers to a monovalent unsaturated aromatic carbocyclic group having a single ring (e.g., phenyl) or multiple condensed rings (e.g., naphthyl or anthryl), which can optionally be unsubstituted or substituted with, for example, halogen, alkyl, alkoxy, mercapto (—SH), alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

"Calpain mediated physiological damage" refers to pathological conditions mediated by calpain. Such conditions can include a variety of ischemic events (such as myocardial or cerebral ischemia), as well as non-ischemic disorders (such as Alzheimer's disease or muscular dystrophy).

"Carbonyl containing group" refers to any substituent containing a carbon-oxygen double bond, including substituents based on —COR where R is an alkyl, lower alkyl, hydroxyl, or a secondary, tertiary, or quaternary amine. The term also encompasses oximes and hydrazones. Alternatively, "carbonyl-containing group" refers to —$R_1COR_2$ groups wherein $R_2$ is alkyl, lower alkyl, hydroxyl, or secondary, tertiary, or quaternary amine and $R_1$ is alkylene, such as methylene (—$CH_2$—). Examples include —COOH, —$CH_2COOH$, —$CH_2COOCH_3$, —$CH_2CONH_2$, and —$CH_2CON(CH_3)_2$.

"Carboxyl" refers to the radical —COOH, and substituted carboxyl refers to —COR where R is alkyl, lower alkyl or a carboxylic acid or ester.

The term "cycloalkyl" refers to an aliphatic ring having 3 to 7 carbon atoms including, but not limited to, cyclopropyl, cyclopentyl, and cyclohexyl.

The term "cycloalkylalkyl" refers to a cycloalkyl group appended to a lower alkyl radical, including, but not limited to, cyclohexylmethyl.

The term "cycloalkenyl" refers to an aliphatic ring having 5 to 7 carbon atoms and also having one carbon-carbon double bond including, but not limited to, cyclopentenyl and cyclohexenyl.

The term "cycloalkenyalkyl" refers to a cycloalkenyl group appended to a lower alkyl radical including, but not limited to, cyclopentenylmethyl and cyclohexenylmethyl.

The term "dialkylamino" refers to —N—$R_1$—$R_2$ wherein $R_1$ and $R_2$ are independently selected from lower alkyl groups.

The term "dialkylaminoalkyl" refers to —N—$R_1$—$R_2$, which is appended to a lower alkyl radical, wherein $R_1$ and $R_2$ are independently selected from lower alkyl groups.

The term "halo" or refers to fluoro, bromo, chloro and iodo substituents. The term "halogen" refers to fluorine, bromine, chlorine, and iodine.

A "heart attack" is a general term encompassing cardiac traumas or diseases, such as myocardial infarction, angina, or cardiac arrhythmia. It is often, but not invariable, the result of cardiovascular disease, such as that seen in atherosclerosis.

The term "heterocycle" (or "heterocyclic") refers to a monovalent saturated, unsaturated, or aromatic carbocyclic group having a single ring (e.g. benzyl, morpholino, pyridyl, or furyl), or multiple condensed rings (e.g. naphthyl, quinolinyl, indolizinyl or benzo[b]thienyl), and having at least one heteroatom, (defined as N, O, P, or S) within the ring. A heterocycle can optionally be unsubstituted or substituted with, for example, halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality. Examples include, but are not limited to, aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl, and pyrazinyl.

The term "(heterocyclic)alkyl" as used herein refers to a heterocyclic group appended to a lower alkyl radical including, but not limited to, pyrrolidinylmethyl and morpholinylmethyl.

"HIV disease" refers to a well recognized constellation of signs and symptoms (including the development of opportunistic infections) in persons who are infected by a human immunodeficiency virus (HIV), as determined by antibody or western blot studies. Laboratory findings associated with this disease are a progressive decline in T-helper cells.

"HIV protease inhibitor" refers to compounds which inhibit the enzymatic activity of an HIV protease. Examples include, but are not limited to, the HIV protease inhibitors disclosed in Table 1.

"Hydroxyl" (or "hydroxy") refers to —OH.

"Hydroxyalkyl" refers to —R—OH, wherein R is alkylene, especially lower alkylene (for example in methylene, ethylene or propylene). A hydroxyalkyl group may be either linear or branched, such as 1-hydroxyisopropyl.

"Ischemia" refers to a low oxygen state of a cell or tissue usually due to obstruction of the arterial blood supply or inadequate blood flow leading to hypoxia. Causes of ischemia include, but are not limited to, vasoconstriction or blockage of a blood vessel. An "ischemic event" is a discrete occurrence producing ischemia, such as a thrombosis, cardiac arrhythmia, or myocardial infarction.

The term "lower alkyl" refers to a cyclic, branched or straight chain monovalent alkyl radical of one to five carbon atoms. This term is further exemplified by such radicals as methyl, ethyl, n-propyl, i-propyl, n-butyl, t-butyl, i-butyl (or 2-methylpropyl), sec-butyl, n-pentyl, cyclopropylmethyl, i-amyl, n-amyl, n-pentyl, 1-methylbutyl, 2,2-dimethylbutyl, 2-methylpentyl, 2,2-dimethylpropyl, n-hexyl. Lower alkyl groups can be unsubstituted or substituted. One specific example of a substituted alkyl is 1,1-dimethyl propyl.

The term "lower alkenyl" refers to a straight or branched chain alkyl radical containing from 2 to 6 carbon atoms and also having one carbon-carbon double bond including, but not limited to, vinyl, 2-propenyl, 2-methyl-2-propenyl, 3-butenyl, 4-pentenyl, and 5-hexenyl.

A "mammal" includes both human and non-human mammals.

The term "N-protecting group" or "N-protected" refers to those chemical groups intended to protect the N-terminus of an amino acid or peptide, or to protect an amino group against undesirable reactions during synthetic procedures. Commonly used N-protecting groups are disclosed in Greene, *Protective Groups In Organic Synthesis* (John Wiley & Sons, New York (1981)). N-protecting groups include: acyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, and 4-nitrobenzoyl; sulfonyl groups, such as benzenesulfonyl, and p-toluenesulfonyl; carbamate forming groups, such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, and phenylthiocarbonyl; alkyl groups, such as benzyl, triphenylmethyl, and benzyloxymethyl; and silyl groups, such as trimethylsilyl.

The term "O-protecting group" refers to a substituent which protects hydroxyl groups against undesirable reactions during synthetic procedures, such as those O-protecting groups disclosed in Greene, *Protective Groups In Organic Synthesis* (John Wiley & Sons, New York (1981)). O-protecting groups include: substituted methyl ethers, such as methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, such as 2,2,2-trichloroethyl; silyl ethers, such as trimethylsilyl, t-butyldimethylsilyl and t-butyldiphenylsilyl; and esters prepared by reacting the hydroxyl group with a carboxylic acid, such as acetate, propionate, and benzoate.

A "pharmaceutical agent," "pharmaceutical composition," or "drug" refers to a chemical compound or composition capable of inducing a desired therapeutic or prophylactic effect when properly administered to a subject. The pharmaceutically acceptable salts of the compounds disclosed herein include, but are not limited to, those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, for example by reacting the free acid with a suitable organic or inorganic base. Any compound disclosed herein may alternatively be administered as a pharmaceutically acceptable salt thereof.

The term "phenyl" refers to a phenyl group, which may be unsubstituted or substituted with a substituent selected from lower alkyl, alkoxy, thioalkoxy, hydroxy and halo.

The term "phenylalkyl" refers to a phenyl group appended to a lower alkyl radical including, but not limited to, benzyl, 4-hydroxybenzyl, 4-chlorobenzyl, and 1-naphthylmethyl.

The term "prodrug" refers to a compound that is converted within the body to a more active form that has medicinal or therapeutic effects.

The term "stable compound" refers to a compound that is sufficiently stable to survive isolation to a useful degree of purity from a reaction mixture and formulation into a therapeutic dosage form suitable for administration.

The term "subject" includes both human and veterinary subjects such as primates, canines, felines, and rodents.

The term "therapeutically effective amount" refers to an amount or dose sufficient to inhibit the enzymatic activity of a calpain and is capable of relieving symptoms associated with calpain activation.

The term "thioalkoxyalkyl" refers to a thioalkoxy group appended to a lower alkyl radical.

Other chemistry terms herein are used according to conventional usage in the art, as exemplified by *The McGraw-Hill Dictionary of Chemical Terms* (1985) and *The Condensed Chemical Dictionary* (1981).

All chemical compounds include both the (+) and (−) stereoisomers, as well as either the (+) or (−) stereoisomer.

HIV Protease Inhibitors

HIV protease inhibitors may be divided into five general classes:

1. hydroxyethylene or dihydroxyethylene isotere state analogs;
2. hydroxyethylamine isotere analogs;
3. C2 symmetry-based inhibitors;
4. (R)-(hydroxyethyl) urea isotere analogs; and
5. nonpeptide HIV protease inhibitors.

Particular, cornmonly known HIV protease inhibitors are listed in Table 1.

The term "HIV protease inhibitor" includes analogs of compounds disclosed herein (such as ritonavir and related compounds disclosed in U.S. Pat. No. 5,541,206; saquinavir and related compounds disclosed in U.S. Pat. No. 5,196,438; indinavir and related compounds disclosed in U.S. Pat. No. 5,413,999; nelfinavir and related compounds disclosed in U.S. Pat. No. 5,484,926; and amprenavir and related compounds disclosed in WO 98/56781). Analogs of HIV protease inhibitors include those compounds that inhibit calpain activity, regardless of their activities against HIV protease. Therefore, the term "HIV protease inhibitor analog" describes a class of compounds, and does not provide a functional limitation on any compound described herein.

TABLE 1
Representative HIV protease Inhibitors
Ritonavir
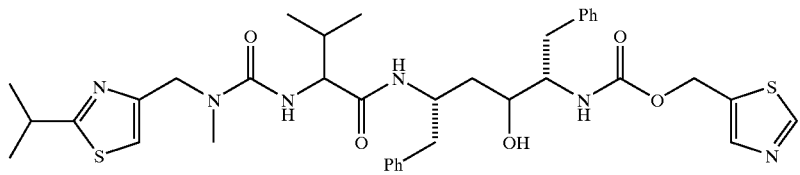
Saquinavir
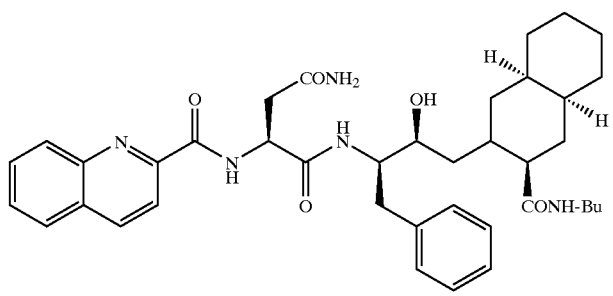
Indinavir
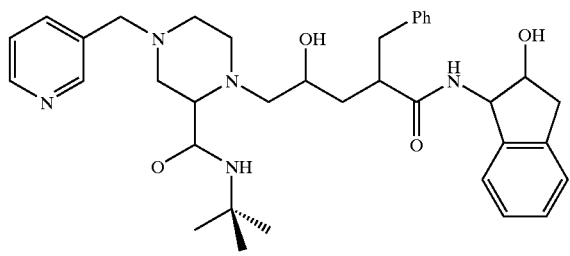
Nelfinavir
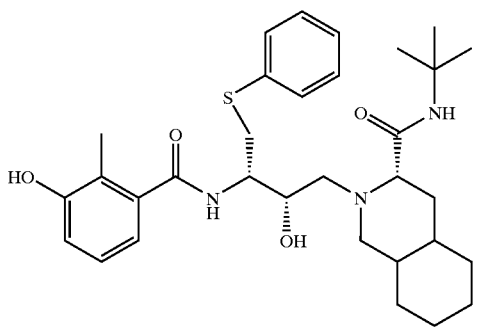
VX-478
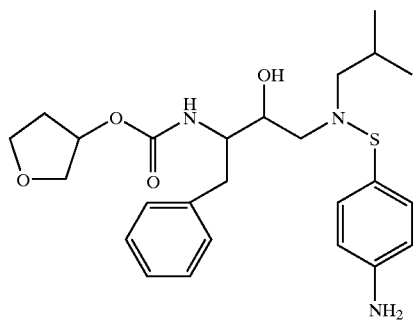

TABLE 1-continued

Representative HIV protease Inhibitors

XM-323

Amprenavir

Ritonavir

The chemical structures of ritonavir and related compounds, including ritonavir analogs, are disclosed in Kempf et al.'s U.S. Pat. No. 5,541,206, herein incorporated by reference.

Ritonavir and related compounds include compounds of the formula:

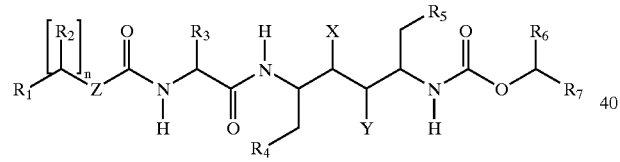

wherein

R$_1$ is monosubstituted thiazolyl, monosubstituted oxazolyl, monosubstituted isoxazolyl, or monosubstituted isothiazolyl; and wherein the substituent is selected from: lower alkyl; lower alkenyl; cycloalkyl; cycloalkylalkyl; cycloalkenyl; cycloalkenylalkyl; heterocyclic, wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl, and pyrazinyl; and wherein the heterocyclic is unsubstituted or substituted with a substituent selected from halo, lower alkyl, hydroxy, alkoxy, and thioalkoxy; (heterocyclic)alkyl, wherein the heterocyclic is defined as above; alkoxyalkyl; thioalkoxyalkyl; alkylamino; dialkylamino; phenyl, wherein the phenyl ring is unsubstituted or substituted with a substituent selected from halo, lower alkyl, hydroxy, alkoxy and thioalkoxy; phenylalkyl, wherein the phenyl ring is unsubstituted or substituted with a substituent selected from halo, lower alkyl, hydroxy, alkoxy and thioalkoxy; dialkylaminoalkyl; alkoxy; or thioalkoxy;

n is 1, 2 or 3;

R$_2$ is hydrogen or a lower alkyl;

R$_3$ is lower alkyl;

R$_4$ and R$_5$ are independently selected from phenyl, thiazolyl, and oxazolyl, wherein the phenyl, thiazolyl or oxazolyl ring is unsubstituted or substituted with a substituent selected from halo, lower alkyl, hydroxy, alkoxy, or thioalkoxy;

R$_6$ is hydrogen or lower alkyl;

R$_7$ is thiazolyl, oxazolyl, isoxazolyl or isothiazolyl, wherein the thiazolyl, oxazolyl, isoxazolyl or isothiazolyl ring is unsubstituted or substituted with lower alkyl;

X is hydrogen and Y is —OH, or X is —OH and Y is hydrogen, with the proviso that X is hydrogen and Y is —OH when Z is —N(R$_8$)— and R$_7$ is unsubstituted; and with the proviso that X is hydrogen and Y is —OH when R$_3$ is methyl and R$_7$ is unsubstituted; and Z is absent, —O—, —S—, —CH$_2$— or —N(R$_8$)— wherein R$_8$ is a lower alkyl, cycloalkyl, —OH or —NHR$_9$, wherein R$_9$ is hydrogen, lower alkyl, or an N-protecting group.

Ritonavir, specifically, is chemically designated as 10-hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5R*,8R* 10R* 11R*)], has a molecular formula of C$_{37}$H$_{48}$N$_6$O$_5$S$_2$, and can be represented by structural formula presented in Table 1. Ritonavir is available from Abbott Laboratories, Inc., under the product name NORVIR.®

Saquinavir

The chemical structures of saquinavir and related compounds, including saquinavir analogs, are disclosed in Martin et al.'s U.S. Pat. No. 5,196,438, herein incorporated by reference.

Saquinavir and related compounds include compounds of the formula:

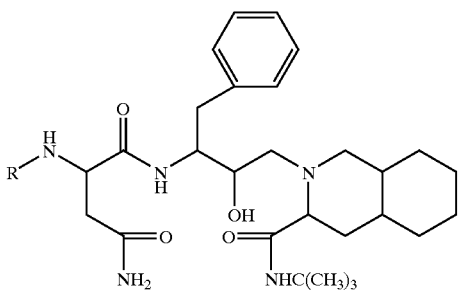

wherein R is benzyloxycarbonyl or 2-quinolylcarbonyl. Saquinavir and related compounds may have stereochemical conformations according to the formula:

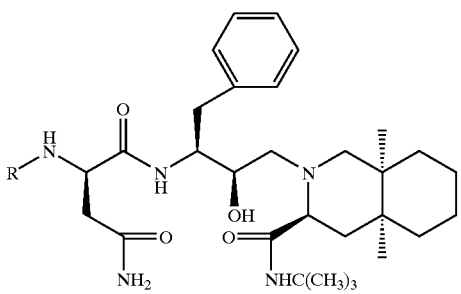

wherein R is benzyloxycarbonyl or 2-quinolylcarbonyl.

Saquinavir, specifically, is chemically designated as N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide with a molecular formula $C_{38}H_{50}N_6O_5$, and can be represented by structural formula presented in Table 1. Saquinavir is available from Roche Laboratories, under the product name FORTOVASE.®

Indinavir

The chemical structures of indinavir and related compounds, including analogs, are disclosed in Vacca et al.'s U.S. Pat. No. 5,413,999, herein incorporated by reference.

Indinavir is chemically designated as [1(1S,2R),5(S)]-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl)-2-(phenylmethyl)-D-erythro-pentonamide sulfate (1:1) salt, with a molecular formula $C_{36}H_{47}N_5O_4 \cdot H_2SO_4$, and can be represented by the structural formula presented in Table 1. Indinavir can be purchased from Merck & Co., Inc., as CRIXIVAN.®

Nelfinavir

The chemical structures of nelfinavir, nelfinavir mesylate, and related compounds, including nelfinavir analogs, are disclosed in Dressman et al.'s U.S. Pat. No. 5,484,926, herein incorporated by reference.

Nelfinavir is chemically designated as [3S-[2(2S*,3s*),3α4aβ8aβ]]-N-(1,1-dimethylethyl)decahydro-2-[2-hydroxy-3-[(3-hydroxy-2-methylbenzoyl)amino]-4-(phenylthio)butyl]-3-isoquinolinecarboxamide. The structural formula of nelfinavir is presented in Table 1, and is commercially available from Agouron Pharmaceuticals, Inc., under the product name VIRACEPT.®

Amprenavir

The chemical structures of amprenavir and related compounds, including amprenavir analogs, are disclosed in Glaxo Group Limited's PCT application WO 98/56781, herein incorporated by reference.

Amprenavir is chemically designated as [3S-[3R*(1R*,2S*)]]-[3-[[(4-aminophenyl)sulfonyl][(2-methylpropyl)amino]-2-hydroxy-1-(phenylmethyl)propyl]-tetrahydro-3-furanyl ester. Amprenavir can be represented by the structural formula presented in Table 1, and may be purchased from Glaxo Wellcome, Inc., under the product name AGERNASE.®

Inhibiting Calpains

Calpain can be inhibited by contacting at least one calpain with an effective amount of an HIV protease inhibitor, an analog, or other compound disclosed herein, including compounds that inhibit calpain even if HIV protease inhibition is reduced or lacking. These methods may be carried out in vivo or in vitro with cells, tissues, or whole animals; with one or more calpains; and with one or more HIV protease inhibitors, analogs, or related compounds disclosed herein. Additionally, these methods may employ a disclosed compound in combination with another therapeutic agent, such as another calpain inhibitor.

Some embodiments involve inhibiting calpains within particular subjects. In some embodiments, a subject at risk of suffering calpain-mediated physiological damage is first identified and then provided with a calpain inhibitor, such as an HIV protease inhibitor. Identification of an at-risk subject can include diagnosing a subject with a condition associated with calpain induced physiological damage. For example, as a prophylactic measure, a human subject demonstrating signs of an impending stroke may be administered a calpain inhibitor (such as an HIV protease inhibitor) disclosed herein. Identification of an at-risk subject can also include choosing an individual research subject for experimental purposes. For example, a rat or dog may be selected to receive treatment intended to induce a stroke and then administered a calpain inhibitor disclosed herein.

In other embodiments, an HIV protease inhibitor, analog, or related compound is administered to a subject following an actual event implicating activation of calpain, thus putting the subject at risk of suffering calpain-mediated physiological damage. For example, a human subject who recently suffered a cardiovascular ischemic event (e.g., heart attack or stroke) may be administered a therapeutically effective amount of pharmaceutical composition that includes a calpain inhibitor disclosed herein. In many embodiments, a composition is administered within several hours of the event precipitating calpain mediated pathologies.

Other embodiments include treating or preventing calpain-mediated physiological damage in a subject animal, for example, a human. In these embodiments, calpain-mediated physiological damage is treated by providing to a subject a therapeutically effective amount of a pharmaceutical composition. The pharmaceutical composition may include one or more of the calpain inhibitors disclosed herein; pharmaceutically compatible carriers, agents, counterions, adjuvants, or vehicles; another calpain inhibitor (in addition to the calpain inhibitors disclosed herein); or combinations thereof. Although the treatment can be used prophylactically in any patient in a demographic group at risk for calpain-mediated physiological damage, subjects also may be selected using more specific criteria, such as a definitive diagnosis of a particular disease or condition associated with calpain-activation (e.g., angina, cataract, myocardial infarction, stroke), or recognition of calcium activation of calpain within the subject.

Providing a pharmaceutical composition to a subject includes methods of administering that composition. Routes of administration include, but are not limited to, oral and parenteral routes, such as intravenous (IV), intraperitoneal (IP), rectal, topical, ophthalmic, nasal, and transdermal. If orally bioavailable HIV protease inhibitors are used, the pharmaceutical compositions are generally provided or administered in the form of a unit dose in solid, semi-solid, or liquid dosage forms such as tablets, pills, powders, liquid solutions, or liquid suspensions. However, the drugs also may be administered intravenously in any conventional medium for intravenous injection, such as an aqueous saline medium, or in a blood plasma medium. The medium also may contain conventional pharmaceutical adjunct materials, such as pharmaceutically acceptable salts to adjust the osmotic pressure, lipid carriers (e.g., cyclodextrins), proteins (e.g., serum albumin), hydrophilic agents (e.g., methyl cellulose), detergents, buffers, preservatives and the like. A more complete explanation of acceptable pharmaceutical carriers can be found in Remington: The Science and Practice of Pharmacy (19$^{th}$ Edition, 1995) in chapter 95.

Therapeutically effective amounts of compounds can be determined in many different ways, depending on the toxicity of the individual HIV protease inhibitor. In some embodiments, the effective amount provides an inhibition constant, for inhibition of calpain, less than or equal to about 11 $\mu$M under the following conditions: (1) using supernatant extracted from PC12 cells, (2) using N-succinyl-leu-ter 7-amino-4-methylcoumarin as the substrate for calpain activity, with (3) fluorescence measured with a 380 nm excitation filter and 480 nm emission filter, and (4) inhibition determined using enzyme kinetic equations solved using linear regression. One example determination of an effective amount under these conditions is provided below in Example #1—Ritonavir Inhibition.

The therapeutically effective amounts of compounds disclosed herein also may be measured in comparison to other calpain inhibitors. For example, ritonavir inhibits calpain about 20 times more effectively than the orally bioavailable calpain inhibitor, PD150606.

Additionally, certain embodiments can be distinguished from methods of treating chronic HIV infection. The treatment of the present invention can be given to a person who does not need a protease inhibitor, for example someone who is not infected with HIV. Moreover, patients suffering chronic HIV infections who take HIV protease inhibitors generally follow a prolonged treatment regimen. For example, the recommended dosage for NORVIR®, an orally administered ritonavir solution produced by Abbott Laboratories, North Chicago, Ill., is 600 mg b.i.d. and, if used in combination with saquinavir, an optimum dosage of 400 to 600 mg b.i.d. As another example, the recommended dosage for INVIRASE®, an orally administered saquinavir mesylate capsule produced by Roche Laboratories, Inc., Nutley, N.J., is 600 mg t.i.d., taken in combination with a nucleoside analog. Since HIV disease is not yet curable, HIV-positive persons taking these HIV protease inhibitors must follow a prolonged, often life-long, course of daily antiviral therapy.

In contrast, therapeutically effective doses of the calpain inhibitors disclosed herein can be provided to a subject for a much shorter period of time. This period of time may be measured after a diagnosis that the subject is at risk for calpain-mediated physiological damage, or after a particular ischemic event, such as a cardiovascular ischemic event. The duration of treatment may be, for example, less than about a month, two weeks, one week, or even less than about 72 hours. For example, a patient suffering a stroke can be provided a therapeutically effective dose of an HIV protease inhibitor for about 72 hours or less. Alternatively, the therapeutically effective dosage may be provided for a period of time from about 6 to about 72 hours. However, the duration of therapy with the calpain inhibitors disclosed herein can also be prolonged, for example, in the treatment of chronic angina or recurrent transient ischemic attacks (TIA's). Moreover, administration can be repeated, but intermittent (for example, following an episode of angina or TIA), even though intermittent or episodic administration would be avoided in an antiviral treatment because it could lead to the development of viral drug resistance.

The specific dose level, frequency of dosage, and duration of treatment for any particular subject may be varied and will depend upon a variety of factors, including: the activity of the specific pharmaceutical composition; the metabolic stability and length of action of that composition; the age, body weight, general health, gender, diet, and other characteristics of the subject; mode and time of administration; the rate of excretion; drug combination parameters; and severity of the condition of the subject undergoing treatment.

The pharmaceutical compositions can be used in the treatment of a variety of conditions or diseases associated with calpain activation, including conditions or diseases caused by or mediated by enzymatically active calpains. Examples of conditions or diseases associated with calpain-mediated physiological damage include, but are not limited to, neurological conditions such as cerebral trauma, spinal cord trauma, subarachnoid hemmorrhage, Alzheimer's disease, alcohol-induced brain damage, muscular dystrophy; as well as non-neurological conditions, such as cataract, coronary atherosclerosis, restenosis, and arthritis. Post-ischemic calpain activation also may be associated with a cardiovascular ischemic event such as, for example, myocardial infarction, angina, cardiac trauma, arhythmia, stroke, thrombosis, or thrombotic platelet aggregation. The trauma or condition leading to the calpain-mediated physiological damage may be induced or accidental.

While the present invention is described in connection with at least one preferred embodiment, the scope of the present invention is not intended to be limited to any particular embodiment. Instead, the descriptions and examples disclosed are intended to cover all alternatives, modifications, and equivalents that may be included within the spirit and scope of the invention as defined by the claims.

EXAMPLES

The following examples are provided to illustrate particular features of various described embodiments. The scope of the present invention should not be limited to those features exemplified.

Example 1

Ritonavir Inhibition of Calpain in PC12 Cell Extracts

Using standard experime ntal methods, ritonavir was unexpectedly found to competitively inhibit calpain with an inhibition constant of about 11 $\mu$M.

PC12 Cell Preparation

PC12 cells were grown in an RPMI solution containing 5% fetal bovine serum, 10% heat-inactivated horse serum, and 50 mg/L gentamicin. Cells were isolated by centrifulgation, and cell pellets suspended in 1 mL of extract buffer, containing 30 mM TRIS at pH 6.8, 15 mMEDTA, 5 mMEGTA, 1 mMDTT, 0.5 M PMSF, 0.1 mg/mL AEBSF, 14.4 mM 2-mercaptoethanol, and 1% triton x-100. After 1 cycle of freeze-thaw, the cell extract was centrifuged at 4° C. at 14,000 g for 20 minutes. The supernatant was removed and assayed.

Fluorescence Assay

Calpain activity was measuring using N-succinyl-leu-tyr 7-amino-4-methylcoumarin as the specific peptide substrate. Fluorescence was measured in a 96-well microplate format (Dyrex Technologies (UK), Middlesex) with a 380 nm excitation filter and 480 nm emission filter. Total volume for each well was 300 μL containing Hanks' Balanced Salt Solution 1× (Cellgro), 2 μM calcium chloride, and varying amounts of inhibitor and N-succinyl-ley-tyr-7-amino-4-methylcoumarin.

Data consisting of relative fluorescence units (RFU) was obtained every two minutes for 1 hour. Data was analyzed based on initial rate, defined as the slope of the increase of the obtained RFU value up to a maximum length of 10 minutes. Data from seven separate experiments performed was used for the analysis. Each experimental point resulted from the mean of the six estimates. Within each experiment, maximal rate of the μ-calpain and m-calpain isoforms was obtained in the presence of 8 mM calcium. Four different substrate concentrations (0 μM, 1 μM, 10 μM, 100 μM) were tested.

Kinetic Analysis

Steady-state kinetic data were fit to a series of equations describing competitive, noncompetitive, and uncompetitive inhibition using non-linear regression, for example the NLREG computer software program, which is available from SoftSeek.com and performs function error minimization using a Newton-Gauss algorithm. Model sufficiency was evaluated based on whether the objective function converged with a tolerance factor of $1 \times 10^{-10}$, the overall F-value for the regression, and the magnitude and sign of the parameters obtained after convergence.

Since cell extracts may have contained slightly different amounts of enzyme activity, kinetic parameters were estimated based on the ratio r:

$$r = \frac{v_i}{v_m} \quad \text{Formula (1)}$$

where $v_i$ is the velocity in the presence of inhibitor, and $v_m$ is the velocity in absence of inhibitor.

For a competitive inhibitor, the initial reaction velocity from steady-state kinetics is:

$$v = \frac{V_{max}}{\left[1 + \left(\frac{K_a}{A}\right) \times \left(1 + \frac{I}{K_i}\right)\right]} \quad \text{Formula (2)}$$

where v=initial velocity $$K_i = \frac{(E)(I)}{(EI)}$$

E=concentration of enzyme
I=concentration of inhibitor
A=substrate concentration
$K_a$=Michaelis-Menten constant The maximal rate occurs in the absence of inhibitor:

$$V_m = \frac{V_{max}}{\left(1 + \frac{K_a}{A}\right)} \quad \text{Formula (3)}$$

A ratio, r, between the observed velocity in the presence of the inhibitor and the velocity in the absence of the inhibitor, where $0 < r \leq 1$, can be determined:

$$r = \frac{V_i}{V_m} \frac{\frac{V_{max}}{\left[1 + \frac{K_a}{A} \times \left(1 + \frac{I}{K_i}\right)\right]}}{\frac{V_{max}}{\left[1 + \frac{K_a}{A}\right]}} \quad \text{Formula (4)}$$

This equation reduces to:

$$r = \frac{A + K_a}{A + K_a\left(1 + \frac{I}{K_i}\right)} \quad \text{Formula (5)}$$

Uncompetitive can be expressed as:

$$r = \frac{A + K_a}{A\left(1 + \frac{I}{K_1}\right)} + K_a \quad \text{Formula (6)}$$

where $K_i$ in Formula (6) is the dissociation constant for the enzyme-substrate-inhibitor complex.

For noncompetitive inhibition, the equation is:

$$r = \frac{A + K_a}{A\left(1 + \frac{I}{K_{ii}}\right) + K_{ia}\left(1 + \frac{I}{K_{is}}\right)} \quad \text{Formula (7)}$$

where $K_{ia}$ is the dissociation constant of the enzyme-substrate complex and $K_{ii}$ is the dissociation constant of the enzyme-substrate-inhibitor complex.

Calpain specific activity was obtained by subtracting the rate obtained in the presence of calcium from the rated obtained in the absence of calcium. In these cell extracts, the observed kinetic parameters represent aggregate estimates since both calpain isoforms were present.

Results

The best model fit was found to occur with the competitive inhibitor model, having an overall F-value of 118.48 with an associated $p \leq 0.00001$. The observed $K_i$ for ritonavir was (mean±standard error of the mean) 11.0±7.0 μM. The observed $K_a$ was 0.4±0.3 mM. The two other possible models for inhibition—noncompetitive and uncompetitive inhibition—were rejected as the parameters failed to converge, or converged to negative values.

Example 2

Ritonavir Inhibition of Calpain in Whole PC12 Cells

The inhibition constant for ritonavir was measured in whole PC12 cells in a manner similar to that described in Example #1. Whole cell enzymatic activity was measured as previously described in DePetrillo, Neurochem. 68:1863–69 (1997). The same four inhibitor concentrations were tested, but the substrate concentration was held at 80 μM. As in Example #1, calpain specific activity was obtained by subtracting the rate obtained in the presence of calcium from the rated obtained in the absence of calcium.

When calpain inhibition by ritonavir was examined in whole PC12 cells with a calcium concentration of 1.4 mM in the presence of 10 $\mu$M ionomycin, competitive inhibition was found, with $K_i$=3.0 $\mu$M (i.e., for m-calpain activation). At calcium concentrations of 0.14 mM, Ki=7.7 $\mu$M (i.e., for $\mu$-calpain activation).

Example 3

Survival of Hippocampal Primary Neurons

Using standard experimental methods, ritonavir was unexpectedly found to increase survival of hippocampal primary neurons exposed to 4-hydroxynonenal (HNE) induced oxidative stress.

Hippocampal Primary Neuron Culture

Hippocampal primary neuron cell cultures were prepared according to the methods described by Mattson, et al., Methods Cell Biol., 46:187–216 (1995). Hippocampi were obtained from rat embryos and incubated for 15 minutes in a solution of 2 mg/ml trypsin in Hank's Balanced Salt Solution (HBSS) containing 2.4 g/l N-[2-hydroxyethyl] piperazine-N'-[2-ethanesulfonic acid] (HEPES) and 10 mg/l gentamicin, pH 7.2 at a concentration of 2 hippocampi/ml. The hippocampi were then rinsed three times in 10 ml of HBSS and incubated for 5 min. in a solution of 1 mg trypsin inhibitor/ml of HBSS. Finally, the cells were rinsed three times with 10 ml of HBSS.

Cells were dissociated by trituration through the narrowed bore of a fire-polished Pasteur pipette and distributed to 35 mm polyethylenimine-coated plastic culture dishes containing 1 ml of MEM+. MEM+ consisted of Minimum Essential Medium (MEM) supplemented with 10% heat inactivated-fetal bovine serum, 10 mM sodium bicarbonate, 20 mM KCl, 1 mM pyruvate, 0.5 mM glutamine, 10 g/l glucose, and 10 mg/l gentamicin at pH 7.2. After a 4 hour incubation at 37° C. in humidified 6% $CO_2$/94% room air, MEM+was replaced with B-27-supplemented Neurobasal medium. Cultures were maintained in this medium for 7 days until this analysis was performed.

Hippocampal Neuron Survival Assay

The effect of ritonavir on hippocampal neuronal survival against HNE toxicity was evaluated in primary cultures when the cultures were 8 days old. Ritonavir was prepared in dimethysulfoxide (DMSO) at a stock concentration of 10 mM. HNE was freshly prepared in Locke's solution at the stock concentration of 1 mM. The Locke's solution consisted of 154 mM NaCl, 5.6 mM KCl, 2.3 mM $CaCl_2$, 1.0 mM $MgCl_2$, 3.6 mM $NaHCO_3$, 5 mM glucose, 5 mM HEPES, 0.01 mg/ml phenol red, at pH 7.2.

Ritonavir was assayed at the following concentrations: 1 pM, 10 pM, 100 pM, 1 nM, and 10 nM in Locke's solution. The final concentration of HNE was 1 mM. The effect of ritonavir alone on hippocampal neuron survival was examined at the each of the above concentrations. The cytoprotective effect of ritonavir also was evaluated in combination with 1 mM HNE. For the combination of ritonavir and HNE, the culture was pre-treated with ritonavir at least 15 min. prior to adding HNE solution. The control cultures without ritonavir or HNE were treated with Locke's solution containing 10 nM of DMSO to match the DMSO content in ritonavir-treated cultures. Four dishes were examined for each of the groups.

Each of the cultures was photographed with phase-contrast inverted Zeiss microscope attached with a 35 mm camera at pre-treatment, 24 hours, and 48 hours after treatment at the same location marked by a scratched grid on the bottom of culture dish. Two photos were taken from each of the dishes. Neuronal survival was quantified by counting the number of neurons on each of the photos. Neuronal viability was identified and determined by morphological criteria: viable neurons had phase-bright somas and intact processes while nonviable neurons had phase-dark, vacuolated somas, and fragmented neuritis. The survival rate was calculated for each of the dishes by using the number of surviving neurons at the 24 hour or 48 hour time point divided by the number of surviving neurons at pre-treatment from the same dish.

Effect of Ritonavir on Survival of Hippocampal Primary Neurons

Hippocampal primary neurons maintained in Locke's solution (Control Group) showed a slight time-dependent decrease in survival. Treatment with either HNE, ritonavir, or combination of both significantly affected cell survival in hippocampal primary neurons in a time-dependent manner (Treatment, $F_{11,36}$=5.46, p<0.001; Time, $F_{1,36}$=294.48, p<0.001).

Exposure of the cell cultures to HNE at the concentration of 1 $\mu$M limited neuronal survival. After either a 24 hour or 48 hour exposure period, neuronal survival significantly decreased in HNE-treated culture (p<0.05 as compared to control, ritonavir 1 pM, ritonavir 10 pM, ritonavir 100 pM, and ritonavir 100 pM+HNE).

Ritonavir alone in culture medium induced concentration-dependent effects on neuronal survival. At lower concentrations of 1–100 pM, ritonavir itself had no effect on cell survival as compared to control cells. At higher concentrations of 1 nM, and particularly 10 nM, ritonavir significantly reduced neuronal survival (p<0.05 as compared to control, ritonavir 1 pM, ritonavir 10 pM, ritonavir 100 pM, and ritonavir 100 pM+HNE).

However, ritonavir was strongly cytoprotective in HNE-treated hippocampal primary neurons. The cytoprotection was dose-dependent, as ritonavir at low concentrations of 1 pM exhibited no cytoprotective activity against HNE-induced cytotoxicity. However, at the concentrations of 10 pM, cytoprotective activity emerged, which increased up to concentrations of 100 pM, where the drug significantly protected hippocampal primary neurons against HNE-induced cytotoxicity (p<0.05 as compared to HNE, ritonavir 1 pM+HNE, and ritonavir 10 pM+HNE). The level of cytoprotection was 100% at this dose level—there was no difference between the ritonavir 100 pM+HNE and the control group in cell survival measures.

At doses higher than 100 pM, ritonavir exhibited cytotoxicity, since neuronal survival in both ritonavir 1 nM+HNE and ritonavir 10 nM+HNE was significantly lower than in the control, ritonavir 100 pM+HNE, and ritonavir 1–100 pM groups (p<0.05). Exposure to 10 $\mu$M ritonavir resulted in essentially 100% cell death after 24 hours.

Example 4

Ritonavir Inhibition of Spectrin Breakdown

Spectrin is a specific substrate of calpains and spectrin breakdown has been shown to be associated with neuronal injury, such as after trauma or NMDA-induced neuronal cell injury. In this example, spectrin was used to assay calpain activity in the presence of ritonavir.

To maximally activate both $\mu$-calpain and m-calpain, PC12 cells were exposed to 2 mM $Ca^{2+}$ for fifteen minutes in the presence of 10 μM ionomycin. A western blot of the cell extracts was probed with anti-spectrin antibodies (commercially available from Chemicon International, Inc., of Temecula, Calif.). Undigested spectrin appeared as a band at approximately 240 kD. The spectrin breakdown products appeared at approximately 150 kD, and followed a ladder pattern associated with limited and specific proteolysis.

Ritonavir at a concentration of 0.1 μM was shown to inhibit spectrin breakdown, demonstrating its ability to inhibit calpain-mediated spectrin breakdown.

Example 5

Screening Methods

This example illustrates how compounds disclosed herein may be screened for therapeutic effectiveness. In this particular example, ritonavir is used to treat neuronal damage in rats following induced strokes.

Sixteen adult male and non-pregnant female Sprague-Dawley rats, weighing approximately 300 g each, are divided into four groups of four rats. Group I receives no treatment. Group II is cannulated to induce a stroke, as described below, and orally administered ritonavir. Group III is cannulated, but receives no drug treatment, and Group IV is not cannulated, but is administered ritonavir.

The number of animals provides an error alpha of 0.05 and a beta (power) of 0.80 with an expected treatment effect size of approximately 1.00. The largest difference in the mean area of brain injury is found between the two treatments incorporating surgery and, expressed in standard deviation units, is equal to [mean1−mean2]/(standard deviation units)≧1.00 (calculations performed according to Cohen, *Statistical Power Analysis for the Behavioral Sciences*, 2$^{nd}$ edition (Lawrence Erlbaum Assoc. 1988)).

Drug doses are determined according to the expected blood level of ritonavir after oral administration and the ritonavir $K_i$. To minimize Type II error rates, ritonavir is administered at a higher normalized dose compared to human dosage recommendations.

Duration of drug dosing is determined according to a similar rationale. Ritonavir is administered for about 24 hours longer than previously reported calpain inhibitors, to minimize the possibility of a Type II error. The frequency of drug administration will be every 8 hours for similar reasons.

Ritonavir (15 mg/kg) is orally administered to the rats two hours before the surgical procedure begins, and 10% chloral hydrate (300 mg/kg) is used for anesthesia. The carotid arteries (including the common, external, and internal artery) are surgically exposed, and a siliconized nylon thread is inserted via needle catheter through the external artery into the middle cerebral artery to occlude blood flow in this artery. The thread is left in place for 60 minutes, then withdrawn and the skin sutured.

An artery occlusion time of 60 minutes initiates reproducible brain tissue injury and mimics stroke injury, where reperfusion can sometimes occur spontaneously or by interventional procedures within an hour.

Drug administration continues every 8 hours for three days, for a total of 9 doses. Prior to the last dose, a blood sample of 0.5 mL is obtained from the tail vein of each rat and analyzed for drug concentration.

Seven days after the procedure, all animals are administered a lethal dose of phenobarbital (20 mg/kg), and transcardial perfusion with 120 mL of 0.9% saline and 200 mL 10% buffered formalin. Brains are removed, cut at 2–3 mm, embedded in paraffin, cut into 4–5 μm thick sections, and stained with hematoxylin/eosin and Kluver-Barrera.

The tissue samples are analyzed for differences in brain injury among the four treatment groups.

Example 6

Additional Examples of Calpain Inhibition

Other examples of calpain inhibitors to be tested in accordance with the assays of Examples 1–3 include, but are not limited to, compounds disclosed in U.S. Pat. Nos. 5,541,206 and 5,413,999, such as the following:

N-(2(R)-hydroxy-1(S)-indanyl)-2(R)-phenylmethyl-4(S)-hydroxy-5-(2-(3-(S)-N'-(t-butylcarboxamido)-(4aS,8aS)-decahydroisoquinoline)yl)-pentaneamide;

N-(2(R)-hydroxy-1(S)-indanyl)-2(R)-phenylmethyl(4(S)-hydroxy-5-(1-(4-carbobenzyloxy-2(S)-N'-(t-butylcarboxamido)-piperazinyl))-pentaneamide;

N-(2(R)-hydroxy-1(S)-indanyl)-2(R)-((4-(2-(4-morpholinyl)ethoxy)phenyl)methyl)-4(S)-hydroxy-5-(2-(3(S)-N'-(t-butylcarboxamido)-(4aS,8aS)-decahydroisoquinoline)yl)-pentaneamide;

N-(2(R)-hydroxy-1(S)-indanyl)-2(R)-((4-(2-(4-morpholinyl)ethoxy)phenyl)methyl-4(S)-hydroxy-5-(1-(4-carbobenzyloxy-2(S)-N'-(t-butylcarboxamido)-piperazinyl))-pentaneamide;

N-(2(R)-hydroxy-1(S)-indanyl)-2(R)-((4-((2-hydroxy)-ethoxy)phenyl)methyl)-4(S)-hydroxy-5-(2-(3(S)-N'-(t-butylcarboxamido)-(4aS,8aS)-decahydroisoquinoline)-yl)-pentaneamide;

N-(2(R)-hydroxy-1(S)-indanyl)-2(R)-((4-((2-hydroxy)-ethoxy)phenyl)methyl)-4(S)-hydroxy-5-(1-(4-carbobenzyloxy-2(S)-N'-(t-butylcarboxamido)-piperazinyl))-pentaneamide;

N-(4(S)-3,4-dihydro-1H-2,2-dioxobenzothiopyranyl)-2(R)-phenylmethyl-4(S)-hydroxy-5-(2-(3(S)-N'-(t-butylcarboxamido)-(4aS,8aS )-decahydroisoquinoline)yl)-pentaneamide;

N-(4(S)-3,4-dihydro-1H-2,2-dioxobenzothiopyranyl)-(2(R)-phenylmethyl-4(S)-hydroxy-5-(1-(4-carbobenzyloxy-2(S)-N'-(t-butylcarboxamido)-piperazinyl))-pentaneamide;

N-(2(R)-hydroxy-1(S)-indanyl)-2(R)-phenylmethyl-4(S)-hydroxy-5-(1-(4-(3-pyridylmethyl)-2(S)-N'(t-butylcarboxamido)-piperazinyl))-pentaneamide, alternatively named [1S-[1α[αS*,γR* ,δ(R*)],2α]]-N-(2,3-dihydro-2-hydroxy-1H-inden-1-yl)-2-[[(1,1-dimethylethyl)amino]carbonyl]-γ-hydroxy-α-(phenylmethyl)-4-(3-pyridinylmethyl)-1-piperazinepentaneamide, or N-(1(S)-2,3-dihydro-2(R)-hydroxy-1H-indenyl)-4)S)-hydroxy-2-(R)-phenyl-methyl-5-[4-(3-pyridylmethyl)-2(S)-t-butylcarbamoyl) piperazinyl]pentaneamide;

N-(2(R)-hydroxy-1(S)-indanyl)-2(R)-phenylmethyl-4-(S)-hydroxy-5-(1-(N'-(t-butyl)-4(S)-phenoxyprolineamid)yl)-pentaneamide;

N-(2(R)-hydroxy-1(S)-indanyl)-2(R)-phenylmethyl-4-(S)-hydroxy-5-(1-(N'-t-butyl-4(S)-2-naphthyloxy-prolineamid)yl)-pentaneamide;

N-(2(R)-hydroxy-1(S)-indanyl)-2(R)-phenylmethyl-4-(S)-hydroxy-5-(1-(N'-t-butyl-4(S)-1-naphthyloxy-prolineamid)yl)-pentaneamide;

N-(2(R)-hydroxy-1(S)-indanyl )-2(R)-phenylmethyl-4-(S)-amino-5-(2-(3(S)-N'-(t-butylcarboxamido)-(4aS,8aS)-decahydroisoquinoline)yl)-pentaneamide;

N-(2(R)-hydroxy-1(S)-indanyl)-2(R)-phenylmethyl-4-(S)-hydroxy-5-(1-(4-(3-phenylpropionyl)-2(S)-N'-(t-butylcarboxamido)-piperazinyl))-pentaneamide;

N-(2(R)-hydroxy-1(S)-indanyl)-2(R)-phenylmethyl-4-(S)-hydroxy-5-(1-(4-benzoyl-2(S)-N'-(t-butylcarboxamido)-piperazinyl))-pentaneamide;

N-(2(R)-hydroxy-1(S)-indanyl)-2(R)-phenylmethyl-4-(S)-hydroxy-5-(1-(4-(3-phenylpropyl)-2(S)-N'-(t-butylcarboxamido)-piperazinyl))-pentaneamide;

N-(2(R)-hydroxy-1(S)-indanyl)-2(R)-phenylmethyl-4-(S)-amino-5-(1-(4-carbobenzyloxy-2(S)-N'-(t-butylcarboxamido)-piperazinyl))-pentaneamide;

N-(2(R)-hydroxy-1(S)-indanyl)-2(R)-((4-(2-(4-morpholinyl)ethoxy)phenyl)methyl)-4(S)-hydroxy-5-(1-(N'-(t-butyl)-4(S)-phenoxyprolineamid)yl)-pentaneamide;

N-(2(R)-hydroxy-1(S)-indanyl)-2(R)-((4-(2-(4-morpholinyl)ethoxy)phenyl)methyl)-4(S)-hydroxy-5-(1-(N'-t-butyl-4(S)-2-naphthyloxy-prolineamid)yl)-pentaneamide;

N-(2(R)-hydroxy-1(S)-indanyl)-2(R)-((4-(2-(4-morpholinyl)ethoxy)phenyl)methyl)-4(S)-hydroxy-5-(1-(N'-t-butyl-4(S)-1-naphthyloxy-prolineamid)yl)-pentaneamide;

N-(2(R)-hydroxy-1(S)-indanyl)-2(R)-((4-(2-(4-morpholinyl)ethoxy)phenyl)methyl)-4(S)-amino-5-(2-(3(S)-N'-(t-butylcarboxamido)-(4aS,8aS)-decahydroisoquinoline)yl)-pentaneamide;

N-(2(R)-hydroxy-1(S)-indanyl)-2(R)-((4-(2-(4-morpholinyl)ethoxy)phenyl)methyl)-4(S)-hydroxy-5-(1-(4-(3-phenylpropionyl)-2(S)-N'-(t-butylcarboxamido)-piperazinyl))-pentaneamide;

N-(2(R)-hydroxy-1(S)-indanyl)-2(R)-((4-(2-(4-morpholinyl)ethoxy)phenyl)methyl)-4(S)-hydroxy-5-(1-(4-benzoyl-2(S)-N'-(t-butylcarboxamido)-piperazinyl))-pentaneamide;

N-(2(R)-hydroxy-1(S)-indanyl)-2(R)-((4-(2-(4-morpholinyl)ethoxy)phenyl)methyl)-4(S)-hydroxy-5-(1-(4-(3-phenylpropyl)-2(S)-N'-(t-burylcarboxamido))-piperazinyl)-pentaneamide;

N-(2(R)-hydroxy-1(S)-indanyl)-2(R)-((4-(2-(4-morpholinyl)ethoxy)phenyl)methyl)-4(S)-amino-5-(1-(4carbobenzyloxy-2(S)-N'-(t-butylcarboxamido) piperazinyl)pentaneamide;

N-(2(R)-hydroxy-1(S)-indanyl)-2(R)-((4-((2-hydroxy)-ethoxy)phenyl)methyl)-4(S)-hydroxy-5-(1-(N'-(t-butyl)-4(S)-phenoxyprolineamid)yl)-pentaneamide;

N-(2(R)-hydroxy-1(S)-indanyl)-2(R)-((4-((2-hydroxy) ethoxy)phenyl)methyl)-4(S)-hydroxy-5-(1-(N'-t-butyl-4(S)-2-naphthyloxy-prolineamid)yl)-pentaneamide;

N-(2(R)-hydroxy-1(S)-indanyl)-2(R)-((4-((2-hydroxy)-ethoxy)phenyl)methyl)-4(S)-hydroxy-5-(1-(N'-t-butyl4(S)-1-naphthyloxy-prolineamid)yl)-pentaneamide;

N-(2(R)-hydroxy-1(S)-indanyl)-2(R)-((4-((2-hydroxy) ethoxy)phenyl)methyl)-4(S)-amino-5-(2-(3(S)-N'-(t-butylcarboxamido)-(4aS,8aS)-decahydroisoquinoline)-yl)pentaneamide;

N-(2(R)-hydroxy-1(S)-indanyl)-2(R)-((4-((2-hydroxy)-ethoxy)phenyl)methyl)-4(S)-hydroxy-5-(1-(4-(3-phenylpropionyl)-2(S)-N'-(t-butylcarboxamido)-piperazinyl))pentaneamide;

N-(2(R)-hydroxy-1(S)-indanyl)-2(R)-((4-((2-hydroxy)-ethoxy)phenyl)methyl)-4(S)-hydroxy-5-(1-(4-benzoyl2(S)-N'-(t-butylcarboxamido)-piperazinyl))-pentaneamide;

N-(2(R)-hydroxy-1(S)-indanyl)-2(R)-((4-((2-hydroxy)-ethoxy)phenyl)methyl)-4(S)-hydroxy-5-(1-(4-(3-phenylpropyl)-2(S)-N'-(t-butylcarboxamido))-piperazinyl)-pentaneamide;

N-(2(R)-hydroxy-1(S)-indanyl)-2(R)-((4-((2-hydroxy)-ethoxy)phenyl)methyl)-4(S)-amino-5-(1-(4-carbobenzyloxy-2(S)-N'-(t-butylcarboxamido)-piperazinyl))-pentaneamide;

N-(4(S)-3,4-dihydro-1H-2,2-dioxobenzothiopyranyl)-2(R)-phenylmethyl-4(S)-hydroxy-5-(1-(N'-(t-butyl)-4(S)-phenoxyprolineamid)yl)-pentaneamide;

N-(4(S)-3,4-dihydro-1H-2,2-dioxobenzothiopyranyl)-2-(R)-phenylmethyl-4(S)-hydroxy-5-(1-(N'-t-butyl-4(S)-2-naphthyloxy-prolineamid)yl)-pentaneamide;

N-(4(S)-3,4-dihydro-1H-2,2-dioxobenzothiopyranyl)-2-(R)-phenylmethyl-4(S)-hydroxy-5-(1-(N'-t-butyl-4(S)-1-naphthyloxy-prolineamid)yl)-pentaneamide;

N-(4(S)-3,4-dihydro-1H-2,2-dioxobenzothiopyranyl)-2-(R)-phenylmethyl-4(S)-amino-5-(2-(3(S)-N'-(t-butylcarboxamido)-(4aS,8aS)-decahydroisoquinoline)yl)pentaneamide;

N-(4(S)-3,4-dihydro-1H-2,2-dioxobenzothiopyranyl)-2-(R)-phenylmethyl-4(S)-hydroxy-5-(1-(4-(3-phenylpropionyl)-2(S)-N'-(t-butylcarboxamido)-piperazinyl))pentaneamide;

N-(4(S)-3,4-dihydro-1H-2,2-dioxobenzothiopyranyl)-2-(R)-phenylmethyl-4(S)-hydroxy-5-(1-(4-benzoyl-2(S)-N'-(t-butylcarboxamido)-piperazinyl))-pentaneamide;

N-(4(S)-3,4-dihydro-1H-2,2-dioxobenzothiopyranyl)-2-(R)-phenylmethyl-4(S)-hydroxy-5-(1-(4-(3-phenylpropyl)-2(S)-N'-(t-butylcarboxamido))-piperazinyl)pentaneamide, or (4(S)-3,4-dihydro-1H-2,2-dioxobenzothiopyranyl)-2-(R)-phenylmethyl-4(S)-amino-5-(1-(4-carbobenzyloxy-2-(S)N'-(t-butylcarboxamido)-piperazinyl))-pentaneamide;

(2S,3R,4S,5S)-5-(N-(N-((N-Methyl-N-((2-isopropyl-4-thiazolyl)methyl)amino)carbonyl)alaninyl)amino)-2-(N-((5-thiazolyl)methoxycarbonyl)amino)-3,4-dihydroxy-1,6-diphenylhexane;

(2S,3R,4S,5S)-5-(N-(N-((2-Isopropyl-4-thiazolyl)methoxycarbonyl)valinyl)amino)-2-(N-((5thiazolyl)methoxycarbonyl)amino)-3,4-dihydroxy-1,6-diphenylhexane;

(2S,3R,4S,5S)-5-(N-(N-((2-Isopropyl-4-thiazolyl)methoxycarbonyl)alaninyl)amino)-2-(N-((5-thiazolyl)methoxycarbonyl)amino)-3,4-dihydroxy-1,6-diphenylhexane;

(2S,3R,4S,5S)-5-(N-(N-((2-(1-Pyrrolidinyl)-4-thiazolyl)methoxycarbonyl)valinyl)amino)-2-(N-((5-thiazolyl)methoxycarbonyl)amino)-3,4-dihydroxy-1,6-diphenylhexane;

(2S,3R,4S,5S)-5-(N-(N-((N-Methyl-N-((2-isopropyl-4-oxazolyl)methyl)amino)carbonyl)valinyl)amino)-2-(N-((5-thiazolyl)methoxycarbonyl)amino)-3,4-dihydroxy-1,6-diphenylhexane;

(2S,3R,4S,5S)-5-(N-(N-((N-Methyl-N-((2-isopropyl-4-oxazolyl)methyl)amino)carbonyl)valinyl)amino)-2-(N-((5-oxazolyl)methoxycarbonyl)amino)-3,4-dihydroxy-1,6-diphenylhexane;

(2S,3R,4S,5S)-5-(N-(N-((N-Methyl-N-((2-isopropyl-4-thiazolyl)methyl)amino)carbonyl)valinyl)amino)-2-(N-((5-oxazolyl)methoxycarbonyl)amino)-3,4-dihydroxy-1,6-diphenylhexane;

(2S,3R,4S,5S)-5-(N-(N-((N-Methyl-N-((2-isopropyl-4-thiazolyl)methyl)amino)carbonyl)valinyl)amino)-2-(N-((5-isoxazolyl)methoxycarbonyl)amino)-3,4-dihydroxy-1,6-diphenylhexane;

(2S,3R,4S,5S)-5-(N-(N-((N-Methyl-N-((2-isopropyl-4-oxazolyl)methyl)amino)carbonyl)valinyl)amino)-2-(N-((5-isoxazolyl)methoxycarbonyl)amino)-3,4-dihydroxy-1,6-diphenylhexane;

(2S,3R,4S,5S)-5-(N-(N-((N-Methyl-N-((2-isopropyl-4-thiazolyl)methyl)amino)carbonyl)valinyl)amino)-2-(N-((5-isothiazolyl)methoxycarbonyl)amino)-3,4-dihydroxy-1,6-diphenylhexane;

(2S,3R,4S,5S)-2-(N-(N-((N-Methyl-N-((2-isopropyl-4-thiazolyl)methyl)amino)carbonyl)alaninyl)amino)-5-(N-((5-thiazolyl)methoxycarbonyl)amino)-3,4-dihydroxy-1,6-diphenylhexane;

(2S,3R,4S,5S)-2-(N-(N-((2-Isopropyl-4-thiazolyl)methoxycarbonyl)valinyl)amino)-5-(N-((5-thiazolyl)methoxycarbonyl)amino)-3,4-dihydroxy-1,6-diphenylhexane;

(2S,3R,4S,5S)-2-(N-(N-((2-Isopropyl-4-thiazolyl)methoxycarbonyl)alaninyl)amino)-5-(N-((5-thiazolyl)methoxycarbonyl)amino)-3,4-dihydroxy-1,6-diphenylhexane;

(2S,3R,4S,5S)-2-(N-(N-((2-(1-Pyrrolidinyl)-4-thiazolyl)methoxycarbonyl)valinyl)amino)-5-(N-((5-thiazolyl)methoxycarbonyl)amino)-3,4-dihydroxy-1,6-diphenylhexane;

(2S,3R,4S,5S)-2-(N-(N-((N-Methyl-N-((2-isopropyl-4-oxazolyl)methyl)amino)carbonyl)valinyl)amino)-5-(N-((5-thiazolyl)methoxycarbonyl)amino)-3,4-dihydroxy-1,6-diphenylhexane;

(2S, 3R,4S,5S)-2-(N-(N-((N-Methyl-N-((2-isopropyl-4-oxazolyl)methyl)amino)carbonyl)valinyl)amino)-5-(N-((5-oxazolyl)methoxycarbonyl)amino)-3,4-dihydroxy-1,6-diphenylhexane;

(2S,3R,4S,5S)-2-(N-(N-((N-Methyl-N-((2-isopropyl-4-thiazolyl)methyl)amino)carbonyl)valinyl)amino)-5-(N-((5-oxazolyl)methoxycarbonyl)amino)-3,4-dihydroxy-1,6-diphenylhexane;

(2S,3R,4S,5S)-2-(N-(N-((N-Methyl-N-((2-isopropyl-4-thiazolyl)methyl)amino)carbonyl)valinyl)amino)-5-(N-((5-isoxazolyl)methoxycarbonyl)amino)-3,4-dihydroxy-1,6-diphenylhexane;

(2S,3R,4S,5S)-2-(N-(N-((N-Methyl-N-((2-isopropyl-4-oxazolyl)methyl)amino)carbonyl)valinyl)amino)-5-(N-((5-isoxazolyl)methoxycarbonyl)amino)-3,4-dihydroxy-1,6-diphenylhexane;

(2S,3R,4S,5S)-2-(N-(N-((N-Methyl-N-((2-isopropyl-4-thiazolyl)methyl)amino)carbonyl)valinyl)-5-(N-((5-isothiazolyl)methoxycarbonyl)amino)-3,4-dihydroxy-1,6-diphenylhexane;

(2S,3R,4R,5S)-5-(N-(N-((N-Methyl-N-((2-isopropyl-4-thiazolyl)methyl)amino)carbonyl)alaninyl)amino)-2-(N-((5-thiazolyl)methoxycarbonyl)amino)-3,4-dihydroxy-1,6-diphenylhexane;

(2S,3R,4R,5S)-5-(N-(N-((2-Isopropyl-4-thiazolyl)methoxycarbonyl)valinyl)amino)-2-(N-((5-thiazolyl)methoxycarbonyl)amino)-3,4-dihydroxy-1,6-diphenylhexane;

(2S,3R,4R,5S)-5-(N-(N-((2-Isopropyl-4-thiazolyl)methoxycarbonyl)alaninyl)amino)-2-(N-((5thiazolyl)methoxycarbonyl)amino)-3,4-dihydroxy-1,6-diphenylhexane;

(2S,3R,4R,5S)-5-(N-(N-((2-(1-Pyrrolidinyl)-4-thiazolyl)methoxycarbonyl)valinyl)amino)-2-(N-((5-thiazolyl)methoxycarbonyl)amino)-3,4-dihydroxy-1,6-diphenylhexane;

(2S,3R,4R,5S)-5-(N-(N-((N-Methyl-N-((2-isopropyl-4-oxazolyl)methyl)amino)carbonyl)valinyl)amino)-2-(N-((5-thiazolyl)methoxycarbonyl)amino)-3,4-dihydroxy-1,6-diphenylhexane;

(2S,3R,4R,5S)-5-(N-(N-((N-Methyl-N-((2-isopropyl-4-oxazolyl)methyl)amino)carbonyl)valinyl)amino)-2-(N-((5-oxazolyl)methoxycarbonyl)amino)-3,4-dihydroxy-1,6-diphenylhexane;

(2S,3R,4R,5S)-5-(N-(N-((N-Methyl-N-((2-isopropyl-4-thiazolyl)methyl)amino)carbonyl)valinyl)amino)-2-(N-((5-oxazolyl)methoxycarbonyl)amino)-3,4-dihydroxy-1,6-diphenylhexane;

(2S,3R,4R,5S)-5-(N-(N-((N-Methyl-N-((2-isopropyl-4-thiazolyl)methyl)amino)carbonyl)valinyl)amino)-2-(N-((5-isoxazolyl)methoxycarbonyl)amino)-3,4-dihydroxy-1,6-diphenylhexane;

(2S,3R,4R,5S)-5-(N-(N-((N-Methyl-N-((2-isopropyl-4-oxazolyl)methyl)amino)carbonyl)valinyl)amino)-2-(N-((5-isoxazolyl)methoxycarbonyl)amino)-3,4-dihydroxy-1,6-diphenylhexane;

(2S,3R,4R,5S)-5-(N-(N-((N-Methyl-N-((2-isopropyl-4-thiazolyl)methyl)amino)carbonyl)valinyl)amino)-2-(N-((5-isothiazolyl)methoxycarbonyl)amino)-3,4-dihydroxy-1,6-diphenylhexane;

(2S,3S,4S,5S)-5-(N-(N-((N-Methyl-N-((2-isopropyl-4-thiazolyl)methyl)amino)carbonyl)alaninyl)amino)-2-(N-((5-thiazolyl)methoxycarbonyl)amino)-3,4-dihydroxy-1,6-diphenylhexane;

(2S,3S,4S,5S)-5-(N-(N-((2-Isopropyl-4-thiazolyl)methoxycarbonyl)valinyl)amino)-2-(N-((5-thiazolyl)methoxycarbonyl)amino)-3,4-dihydroxy-1,6-diphenylhexane;

(2S,3S,4S,5S)-5-(N-(N-((2-Isopropyl-4-thiazolyl)methoxycarbonyl)alaninyl)amino)-2-(N-((5-thiazolyl)methoxycarbonyl)amino)-3,4-dihydroxy-1,6-diphenylhexane;

(2S,3S,4S,5S)-5-(N-(N-((2-(1-Pyrrolidinyl)-4-thiazolyl)methoxycarbonyl)valinyl)amino)-2-(N-((5-thiazolyl)methoxycarbonyl)amino)-3,4-dihydroxy-1,6-diphenylhexane;

(2S,3S,4S,5S)-5-(N-(N-((N-Methyl-N-((2-isopropyl-4-oxazolyl)methyl)amino)carbonyl)valinyl)amino)-2-(N-((5-thiazolyl)methoxycarbonyl)amino)-3,4-dihydroxy-1,6-diphenylhexane;

(2S,3S,4S,5S)-5-(N-(N-((N-Methyl-N-((2-isopropyl-4-oxazolyl)methyl)amino)carbonyl)valinyl)amino)-2-(N-((5-oxazolyl)methoxycarbonyl)amino)-3,4-dihydroxy-1,6-diphenylhexane;

(2S,3S,4S,5S)-5-(N-(N-((N-Methyl-N-((2-isopropyl-4-thiazolyl)methyl)amino)carbonyl)valinyl)amino)-2-(N-((5-oxazolyl)methoxycarbonyl)amino)-3,4-dihydroxy-1,6-diphenylhexane;

(2S,3S,4S,5S)-5-(N-(N-((N-Methyl-N-((2-isopropyl-4-thiazolyl)methyl)amino)carbonyl)valinyl)amino)-2-(N-((5-isoxazolyl)methoxycarbonyl)amino)-3,4-dihydroxy-1,6-diphenylhexane;

(2S,3S,4S,5S)-5-(N-(N-((N-Methyl-N-((2-isopropyl-4-oxazolyl)methyl)amino)carbonyl)valinyl)amino)-2-(N-((5-isoxazolyl)methoxycarbonyl)amino)-3,4-dihydroxy-1,6-diphenylhexane;

(2S,3S,4S,5S)-5-(N-(N-((N-Methyl-N-((2-isopropyl-4-thiazolyl)methyl)amino)carbonyl)valinyl)amino)-2-(N-((5-isothiazolyl)methoxycarbonyl)amino)-3,4-dihydroxy-1,6-diphenylhexane;

(2S,3S,5S)-5-(N-(N-((N-Methyl-N-((2-cyclopentyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-cyclohexyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(1,1-dimethyl)ethyl-4-thiazolyl)methyl)-amino)carbonyl)valinyl)amino)-2-(N-((5-oxazolyl) methoxycarbonyl)amino)1,6-diphenyl-3-hydroxyhexane;

(2S,3S,5S)-5-(N-(N-((N-Methyl-N-((2-cyclobutyl-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-cyclopropyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-ethyl-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-ethenyl-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(2-propenyl)-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(1-cyclopentenyl)-4-thiazolyl)-methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(1-cyclohexenyl)-4-thiazolyl)methyl)amino)carbonyl)valinyl)-2-(N-((5-oxazolyl)methoxycarbonyl)amino)-1,6-diphenyl-3-hydroxyhexane;

(2S,3S,5S)-5-(N-(N-((N-Methyl-N-((4-cyclopentenyl-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((4-cyclohexenyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(3-propenyl)-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(1-propenyl)-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-N-((N-Methyl-N-((2-(1-methyl-1-propenyl)-4-thiazolyl)methyl)-amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(2-methyl-1-propenyl)-4-thiazolyl)-methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(1,2-dimethyl-1-propenyl)-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(cyclopentyl)methyl-4-thiazolyl)methyl)-amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(cyclohexyl)methyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-phenyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-benzyl-4-thiazolyl)methyl)amino)-carbonyl)valinyl)amino)-2-(N-((5-oxazolyl)methoxycarbonyl)amino)-1,6-diphenyl-3-hydroxyhexane;

(2S ,3S,5S)-5-(N-(N-((N-Methyl-N-((2-(2-phenyl)ethyl-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(2-phenyl-1-ethenyl)-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(4-fluoro)phenyl-4-thiazolyl)methyl)-amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(2-chloro)phenyl-4-thiazolyl)methyl)-amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(3-methoxy)phenyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(2-thiazolyl)-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(2-thiazolyl)methyl-4-thiazolyl)methyl)-amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-methoxy-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-ethoxy-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-isopropyloxy-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(N,N-dimethylamino)methyl-4-thiazolyl)-methyl)amino)carbonyl)valinyl)amino)-2-(N-((5-oxazolyl)methoxycarbonyl)-amino)-1,6-diphenyl-3-hydroxyhexane;

(2S,3S,5S)-5-(N-(N-((N-Methyl-N-((2-(1-pyrrolidinyl)methyl-4-thiazolyl)methyl)-amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-propyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(2-methyl)propyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(1-methyl)propyl-4-thiazolyl)methyl)-amino)carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-(1-ethyl)propyl-4-thiazolyl)methyl)amino)-carbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-cyclopentyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-cyclohexyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(1,1-dimethyl)ethyl-4-thiazolyl)methyl)amino)carbonyl)valinyl)amino)-2-(N-((5-isoxazolyl)methoxycarbonyl)amino)1,6-diphenyl-3-hydroxyhexane;

(2S,3S,5S)-5-(N-(N-((N-Methyl-N-((2-cyclobutyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-cyclopropyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-ethyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-ethenyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-2-propenyl)-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(1-cyclopentenyl)-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(1-cyclohexenyl)-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((4-cyclopentenyl-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((4-cyclohexenyl-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(3-propenyl)-4-thiazolyl) methyl) amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(1-propenyl)-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(1-methyl-1-propenyl)-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(2-methyl-1-propenyl)-4-thiazolyl)methyl)amino)carbonyl)valinyl)amino)-2-(N-((5-isoxazolyl)methoxycarbonyl)-amino)-1,6-diphenyl-3-hydroxyhexane;

(2S,3S,5S)-5-(N-(N-((N-Methyl-N-((2-(1,2-dimethyl-1-propenyl)-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(cyclopentyl)methyl-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(cyclohexyl)methyl-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-phenyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-benzyl-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(2-phenyl)ethyl-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(2-phenyl-1-ethenyl)-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(4-fluoro)phenyl-4-thiazolyl)methyl)-amino)carbonyl)valinyl)amino)-2-(N-((5-isoxazolyl)methoxycarbonyl)amino)1,6-diphenyl-3-hydroxyhexane;

(2S,3S,5S)-5-(N-(N-((N-Methyl-N-((2-(2-chloro)phenyl-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(3-methoxy)phenyl-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(2-thiazolyl)-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(2-thiazolyl)methyl-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-methoxy-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-ethoxy-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-isopropyloxy-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(N,N-dimethylamino)methyl-4-thiazolyl)-methyl)amino)carbonyl)valinyl)amino)-2-(N-((5-isoxazolyl)methoxycarbonyl)-amino)-1,6-diphenyl-3-hydroxyhexane;

(2S,3S,5S)-5-(N-(N-((N-Methyl-N-((2-(1-pyrrolidinyl)methyl-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-propyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(2-methyl)propyl-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(1-methyl)propyl-4-thiazolyl)methyl)-amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-(1-ethyl)propyl-4-thiazolyl)methyl)amino)-carbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-cyclopentyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-cyclohexyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(1,1-dimethyl)ethyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-cyclobutyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-cyclopropyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-ethyl-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-ethenyl-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(2-propenyl)-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(1-cyclopentenyl)-4-thiazolyl)-methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(1-cyclohexenyl)-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((4-cyclopentenyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((4-cyclohexenyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(3-propenyl)-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(1-propenyl)-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(1-methyl-1-propenyl)-4-thiazolyl)methyl)-amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(2-methyl-1-propenyl)-4-thiazolyl)-methyl)amino)carbonyl)valinyl)amino)-2-(N-((5-isothiazolyl)methoxycarbonyl)-amino)-1,6-diphenyl-3-hydroxyhexane;

(2S,3S,5S)-5-(N-(N-((N-Methyl-N-((2-(1,2-dimethyl-1-propenyl)-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(cyclopentyl)methyl-4-thiazolyl)methyl)-amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(cyclohexyl)methyl-4-thiazolyl)methyl)-amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-phenyl-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-benzyl-4-thiazolyl)methyl)amino)-carbonyl)valinyl)amino)-2-

(N-((5-isothiazolyl)methoxycarbonyl)amino)-1,6-diphenyl-3-hydroxyhexane;

(2S,3S,5S)-5-(N-(N-((N-Methyl-N-((2-(2-phenyl)ethyl-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(2-phenyl-1-ethenyl)-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(4-fluoro)phenyl-4-thiazolyl)methyl)-amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(2-chloro)phenyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(3-methoxy)phenyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(2-thiazolyl)-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(2-thiazolyl)methyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-methoxy-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-ethoxy-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-isopropyloxy-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(N,N-dimethylamino)methyl-4-thiazolyl)-methyl)amino)carbonyl)valinyl)amino)-2-(N-((5-isothiazolyl)methoxycarbonyl)-amino)-1,6-diphenyl-3-hydroxyhexane;

(2S,3S,5S)-5-(N-(N-((N-Methyl-N-((2-(1-pyrrolidinyl)methyl-4-thiazolyl)methyl)-amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-propyl-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(2-methyl)propyl-4-thiazolyl)methyl)-amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(1-methyl)propyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-(1-ethyl)propyl-4-thiazolyl)methyl)amino)-carbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-isopropyl-4-thiazolyl)methyl)amino)carbonyl)alaninyl)amino)-2-(N-((5-oxazolyl)methoxycarbonyl)amino)-1,6-diphenyl-3-hydroxyhexane;

(2S,3S,5S)-5-(N-(N-((N-Ethyl-N-((2-isopropyl-4-thiazolyl)methyl)amino)carbonyl)valinyl)amino)-2-(N-((5-oxazolyl)methoxycarbonyl)amino)-1,6-diphenyl-3-hydroxyhexane;

(2S,3S,5S)-5-(N-(N-((2-Isopropyl-4-thiazolyl)methoxycarbonyl)valinyl)amino)-2-(N-((5-oxazolyl)methoxycarbonyl)amino)-1,6-diphenyl-3-hydroxyhexane;

(2S,3S,5S)-2-(N-(N-((2-Isopropyl-4-thiazolyl)methoxycarbonyl)valinyl)amino)-5-(N-((5-oxazolyl)methoxycarbonyl)amino)-1,6-diphenyl-3-hydroxyhexane;

(2S,3S,5S)-5-(N-(N-((2-Isopropyl-4-thiazolyl)methoxycarbonyl)alaninyl)amino)-2-(N-((5-oxazolyl)methoxycarbonyl)amino)-1,6-diphenyl-3-hydroxyhexane;

(2S,3S,5S)-5-(N-(N-((2-(N,N-Dimethylamino)-4-thiazolyl)methoxycarbonyl)valinyl)amino)-2-(N-((5-oxazolyl)methoxycarbonyl)amino)-1,6-diphenyl-3-hydroxyhexane;

(2S,3S,5S)-2-(N-(N-((2-(N,N-Dimethylamino)-4-thiazolyl)methoxycarbonyl)valinyl)amino)-5-(N-((5-oxazolyl)methoxycarbonyl)amino)-1,6-diphenyl-3-hydroxyhexane;

(2S,3S,5S)-5-(N-(N-((2-(4-Morpholinyl)-4-thiazolyl)methoxycarbonyl)valinyl)amino)-2-(N-((5-oxazolyl)methoxycarbonyl)amino)-1,6-diphenyl-3-hydroxyhexane;

(2S,3S,5S)-2-(N-(N-((2-(4-Morpholinyl)-4-thiazolyl)-methoxycarbonyl)valinyl)amino)-5-(N-((5-oxazolyl)methoxycarbonyl)amino)-1,6-diphenyl-3-hydroxyhexane;

(2S,3S,5S)-5-(N-(N-((2-(1-Pyrrolidinyl)-4-thiazolyl)methoxycarbonyl)valinyl)amino)-2-(N-((5-oxazolyl)methoxycarbonyl)amino)-1,6-diphenyl-3-hydroxyhexane;

(2S,3S,5S)-2-(N-(N-((2-(1-Pyrrolidinyl)-4-thiazolyl)methoxycarbonyl)valinyl)amino)-5-(N-((5-oxazolyl)methoxycarbonyi)amino)-1,6-diphenyl-3-hydroxyhexane;

(2S,3S,5S)-5-(N-(N-((3-Isopropyl-5-isoxazolyl)methoxycarbonyl)valinyl)amino)-2-(N-((5-oxazolyl)methoxycarbonyl)amino)-1,6-diphenyl-3-hydroxyhexane;

(2S,3S,5S)-5-(N-(N-((N-Methyl-N-((2-isopropyl-4-thiazolyl)methyl)amino)carbonyl)alaninyl)amino)-2-(N-((5-isoxazolyl)methoxycarbonyl)amino)-1,6-diphenyl-3-hydroxyhexane;

(2S,3S,5S)-5-(N-(N-((N-Ethyl-N-((2-isopropyl-4-thiazolyl)methyl)amino)carbonyl)valinyl)amino)-2-(N-((5-isoxazolyl)methoxycarbonyl)amino)-1,6-diphenyl-3-hydroxyhexane;

(2S,3S,5S)-5-(N-(N-((2-Isopropyl-4-thiazolyl)methoxycarbonyl)valinyl)amino)-2-(N-((5-isoxazolyl)methoxycarbonyl)amino)-1,6-diphenyl-3-hydroxyhexane;

(2S,3S,5S)-2-(N-(N-((2-Isopropyl-4-thiazolyl)methoxycarbonyl)valinyl)amino)-5-(N-((5-isoxazolyl)

methoxycarbonyl)amino)-1,6-diphenyl-3-hydroxyhexane;

(2S,3S,5S)-5-(N-(N-((2-Isopropyl-4-thiazolyl)methoxycarbonyl)alaninyl)amino)-2-(N-((5-isoxazolyl)methoxycarbonyl)amino)-1,6-diphenyl-3-hydroxyhexane;

(2S,3S,5S)-5-(N-(N-((2-(N,N-Dimethylamino)-4-thiazolyl)methoxycarbonyl)valinyl)amino)-2-(N-((5-isoxazolyl)methoxycarbonyl)amino)-1,6-diphenyl-3-hydroxyhexane;

(2S,3S,5S)-2-(N-(N-((2-(N,N-Dimethylamino)-4-thiazolyl)methoxycarbonyl)valinyl)amino)-5-(N-((5-isoxazolyl)methoxycarbonyl)amino)-1,6-diphenyl-3-hydroxyhexane;

(2S,3S,5S)-5-(N-(N-((2-(4-Morpholinyl)-4-thiazolyl)methoxycarbonyl)valinyl)amino)-2-(N-((5-isoxazolyl)methoxycarbonyl)amino)-1,6-diphenyl-3-hydroxyhexane;

(2S,3S,5S)-2-(N-(N-((2-(4-Morpholinyl)-4-thiazolyl)methoxycarbonyl)valinyl)amino)-5-(N-((5-isoxazolyl)methoxycarbonyl)amino)-1,6-diphenyl-3-hydroxyhexane;

(2S,3S,5S)-5-(N-(N-((2-(1-Pyrrolidinyl)-4-thiazolyl)methoxycarbonyl)valinyl)amino)-2-(N-((5-isoxazolyl)methoxycarbonyl)amino)-1,6-diphenyl-3-hydroxyhexane;

(2S,3S,5S)-2-(N-(N-((2-(1-Pyrrolidinyl)-4-thiazolyl)methoxycarbonyl)valinyl)amino)-5-(N-((5-isoxazolyl)methoxycarbonyl)amino)-1,6-diphenyl-3-hydroxyhexane;

(2S,3S,5S)-5-(N-(N-((3-Isopropyl-5-isoxazolyl)methoxycarbonyl)valinyl)amino)-2-(N-((5-isoxazolyl)methoxycarbonyl)amino)-1,6-diphenyl-3-hydroxyhexane;

(2S,3S,5S)-5-(N-(N-((N-Methyl-N-((2-isopropyl-4-thiazolyl)methyl)amino)carbonyl)alaninyl)amino)-2-(N-((5-isothiazolyl)methoxycarbonyl)amino)-1,6-diphenyl-3-hydroxyhexane;

(2S,3S,5S)-5-(N-(N-((N-Ethyl-N-((2-isopropyl-4-thiazolyl)methyl)amino)carbonyl)valinyl)amino)-2-(N-((5-isothiazolyl)methoxycarbonyl)amino)-1,6-diphenyl-3-hydroxyhexane;

(2S,3S,5S)-5-(N-(N-((2-Isopropyl-4-thiazolyl)methoxycarbonyl)valinyl)amino)-2-(N-((5-isothiazolyl)methoxycarbonyl)amino)-1,6-diphenyl-3-hydroxyhexane;

(2S,3S,5S)-2-(N-(N-((2-Isopropyl-4-thiazolyl)methoxycarbonyl)valinyl)amino)-5-(N-((5-isothiazolyl)methoxycarbonyl)amino)-1,6-diphenyl-3-hydroxyhexane;

(2S,3S,5S)-5-(N-(N-((2-Isopropyl-4-thiazolyl)methoxycarbonyl)alaninyl)amino)-2-(N-((5-isothiazolyl)methoxycarbonyl)amino)-1,6-diphenyl-3-hydroxyhexane;

(2S,3S,5S)-5-(N-(N-((2-(N,N-Dimethylamino)-4-thiazolyl)methoxycarbonyl)valinyl)amino)-2-(N-((5-isothiazolyl)methoxycarbonyl)amino)-1,6-diphenyl-3-hydroxyhexane;

(2S,3S,5S)-2-(N-(N-((2-(N,N-Dimethylamino)-4-thiazolyl)methoxycarbonyl)valinyl)amino)-5-(N-((5-isothiazolyl)methoxycarbonyl)amino)-1,6-diphenyl-3-hydroxyhexane;

(2S,3S,5S)-5-(N-(N-((2-(4-Morpholinyl)-4-thiazolyl)methoxycarbonyl)valinyl)amino)-2-(N-((5-isothiazolyl)methoxycarbonyl)amino)-1,6-diphenyl-3-hydroxyhexane;

(2S,3S,5S)-2-(N-(N-((2-(4-Morpholinyl)-4-thiazolyl)methoxycarbonyl)valinyl)amino)-5-(N-((5-isothiazolyl)methoxycarbonyl)amino)-1,6-diphenyl-3-hydroxyhexane;

(2S,3S,5S)-5-(N-(N-((2-(1-Pyrrolidinyl)-4-thiazolyl)methoxycarbonyl)valinyl)amino)-2-(N-((5-isothiazolyl)methoxycarbonyl)amino)-1,6-diphenyl-3-hydroxyhexane;

(2S,3S,5S)-2-(N-(N-((2-(1-Pyrrolidinyl)-4-thiazolyl)methoxycarbonyl)valinyl)amino)-5-(N-((5-isothiazolyl)methoxycarbonyl)amino)-1,6-diphenyl-3-hydroxyhexane;

(2S,3S,5S)-5-(N-(N-((3-Isopropyl-5-isoxazolyl)methoxycarbonyl)valinyl)amino)-2-(N-((5-isothiazolyl)methoxycarbonyl)amino)-1,6-diphenyl-3-hydroxyhexane;

(2S,3S,5S)-5-(N-(N-((N-Methyl-N-((2-isopropyl-4-oxazolyl)methyl)amino)carbonyl)valinyl)amino)-2-(N-((5-isothiazolyl)methoxycarbonyl)amino)-1,6-diphenyl-3-hydroxyhexane.

Example 7

Treatment of a Specific Condition

Although a variety of conditions can be treated using a variety of drug regimens as described herein, the following examples provide some specific instances (without limitation) about treatment of some of these conditions.

For the treatment of angina or a transient ischemic attack, 300–600 mg of ritonavir are administered twice a day beginning the day of an attack, continued for 72 hours, and then stopped until the next attack occurs.

In the treatment of more severe ischemia, such as that caused by a myocardial infarction (MI), the same or a lesser dose may be administered for a longer period of time. For example, a compound disclosed herein is administered following initial clinical presentation with signs and symptoms of an MI (such as chest pain and EKG changes), or following laboratory confirmation of the MI (such as presence of elevated cardiac enzyme levels such as CPK-MB). Administration would be continued for at least a week, for example, a month, or in some examples, no more than one or two weeks. Repeated courses of the calpain inhibitor can be given for subsequent MI's or other calpain mediated conditions (such as an ischemic or hemorrhagic stroke).

In yet other conditions, such as the prevention of cataract, treatment may be sustained (for example, 100–300 mg by mouth each day, for example as a single dose) for life, or until extraction of a cataractous crystalline lens.

We claim:

1. A method of inhibiting a calpain, comprising contacting the calpain with an effective amount of an HIV protease inhibitor, or an analog of an HIV protease inhibitor, sufficient to inhibit the calpain.

2. The method according to claim 1, wherein the method is a method of treating a subject, comprising:
   identifying a subject at risk of suffering calpain-mediated physiological damage; and
   providing to the subject at least one HIV protease inhibitor or an analog of an HIV protease inhibitor.

3. The method according to claim 2 wherein the subject is a mammal.

4. The method according to claim 3 wherein the subject is selected from the group consisting of primates, canines, felines, and rodents.

5. The method according to claim 4 wherein the subject is a human.

6. The method according to claim 1, wherein the HIV protease inhibitor, or the analog, is a compound of the formula:

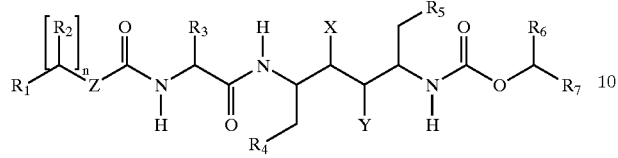

wherein

R₁ is monosubstituted thiazolyl, monosubstituted oxazolyl, monosubstituted isoxazolyl, or monosubstituted isothiazolyl, and wherein the substituent is selected from: lower alkyl; lower alkenyl; cycloalkyl; cycloalkylalkyl; cycloalkenyl; cycloalkenylalkyl; heterocyclic, wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl, and wherein the heterocyclic is unsubstituted or substituted with a substituent selected from halo, lower alkyl, hydroxy, alkoxy and thioalkoxy; (heterocyclic)alkyl, wherein heterocyclic is defined as above; alkoxyalkyl; thioalkoxyalkyl; alkylamino; dialkylamino; phenyl, wherein the phenyl ring is unsubstituted or substituted with a substituent selected from halo, lower alkyl, hydroxy, alkoxy and thioalkoxy; phenylalkyl, wherein the phenyl ring is unsubstituted or substituted with a substituent selected from halo, lower alkyl, hydroxy, alkoxy and thioalkoxy; dialkylaminoalkyl; alkoxy; and thioalkoxy;

n is 1, 2 or 3;

R₂ is hydrogen or lower alkyl;

R₃ is lower alkyl;

R₄ and R₅ are independently selected from phenyl, thiazolyl, and oxazolyl, wherein the phenyl, thiazolyl or oxazolyl ring is unsubstituted or substituted with a substituent selected from halo, lower alkyl, hydroxy, alkoxy, and thioalkoxy;

R₆ is hydrogen or lower alkyl;

R₇ is thiazolyl, oxazolyl, isoxazolyl or isothiazolyl, wherein the thiazolyl, oxazolyl, isoxazolyl or isothiazolyl ring is unsubstituted or substituted with lower alkyl;

X is hydrogen and Y is —OH, or X is —OH and Y is hydrogen, with the proviso that X is hydrogen and Y is —OH when Z is —N(R₈)— and R₇ is unsubstituted, and with the proviso that X is hydrogen and Y is —OH when R₃ is methyl and R₇ is unsubstituted;

Z is absent, —O—, —S—, —CH₂— or —N(R₈)— wherein R₈ is a lower alkyl, cycloalkyl, —OH or —NHR₉ wherein R₉ is hydrogen, lower alkyl or an N-protecting group; and a pharmaceutically acceptable acid addition, salt, ester, or prodrug thereof.

7. The method according to claim 1 wherein the HIV protease inhibitor, or the analog, is a compound of the formula:

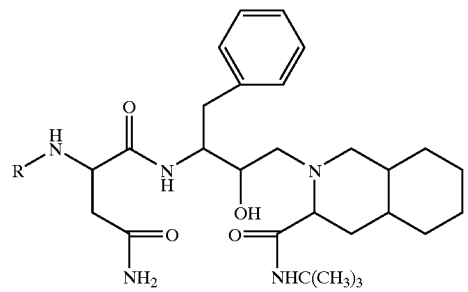

wherein R is benzyloxycarbonyl or 2-quinolylcarbonyl; and a pharmaceutically acceptable acid addition, salt, ester, or prodrug thereof.

8. The method according to claim 1 wherein the HIV protease inhibitor is selected from the group consisting of nelfinavir, ritonavir, saquinavir, indinavir, and amprenavir.

9. The method according to claim 8 wherein the HIV protease inhibitor is selected from the group consisting of ritonavir and saquinavir.

10. The method according to claim 9 wherein the HIV protease inhibitor is ritonavir.

11. The method according to claim 1 wherein the effective amount provides an inhibition constant, $K_i$, for inhibition of calpain, less than or equal to about 11 $\mu$M as measured using supernatant extracted from PC12 cells, N-succinyl-leu-ter-7-amino-4-methylcoumarin as the substrate for calpain activity, with fluorescence measured with a 380 nm excitation filter and 480 nm emission filter, and inhibition determined using enzyme kinetic equations solved by nonlinear regression.

12. The method according claim 1 wherein the HIV protease inhibitor or analog is orally bioavailable.

13. The method according to claim 12 wherein the HIV protease inhibitor or analog inhibits calpain about 20 times more effectively than PD150606, and wherein the inhibition constant for the HIV protease inhibitor is determined using supernatant extracted from PC12 cells, N-succinyl-leu-ter-7-amino-4-methylcoumarin as the substrate for calpain activity, with fluorescence measured with a 380 nm excitation filter and 480 nm emission filter, and inhibition determined using enzyme kinetic equations solved by nonlinear regression.

14. The method according to claim 1 wherein the calpain is located within a cell.

15. The method according to claim 14 wherein the cell is a cardiac cell or nerve cell.

16. A method of treating or inhibiting calpain-mediated physiological damage, comprising administering to a subject a therapeutically effective amount of a pharmaceutical composition comprising an HIV protease inhibitor or an analog of an HIV protease inhibitor, wherein the therapeutically effective amount is sufficient to inhibit the calpain-mediated physiological damage.

17. The method according to claim 16 wherein the calpain-mediated physiological damage is induced by calcium activation of calpain.

18. The method according to claim 16 wherein the calpain-mediated physiological damage is associated with cerebral trauma, spinal cord trauma, subarachnoid hemmorrhage, Alzheimer's disease, alcohol-induced brain damage, muscular dystrophy, cataract, platelet aggregation, restenosis, or arthritis.

19. The method according to claim 16 wherein the calpain-mediated physiological damage is induced by ischemia.

20. The method according to claim 16 wherein the ischemia is a cardiovascular ischemic event which is identified prior to administering the HIV protease inhibitor to the subject.

21. The method according to claim 16 wherein the method is a method of treating or preventing a cardiovascular disease.

22. The method according to claim 16 wherein the subject is a mammal.

23. The method according to claim 22 wherein the subject is selected from the group consisting of primates, canines, felines, and rodents.

24. The method according to claim 23, wherein the subject is a human.

25. The method according to claim 16 wherein the HIV protease inhibitor or analog is a compound of the formula:

[structure]

wherein
$R_1$ is monosubstituted thiazolyl, monosubstituted oxazolyl, monosubstituted isoxazolyl, or monosubstituted isothiazolyl, and wherein the substituent is selected from: lower alkyl; lower alkenyl; cycloalkyl; cycloalkylalkyl; cycloalkenyl; cycloalkenylalkyl; heterocyclic, wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl; and wherein the heterocyclic is unsubstituted or substituted with a substituent selected from halo, lower alkyl, hydroxy, alkoxy and thioalkoxy; (heterocyclic)alkyl, wherein heterocyclic is defined as above; alkoxyalkyl; thioalkoxyalkyl; alkylamino; dialkylamino; phenyl, wherein the phenyl ring is unsubstituted or substituted with a substituent selected from halo, lower alkyl, hydroxy, alkoxy and thioalkoxy; phenylalkyl, wherein the phenyl ring is unsubstituted or substituted with a substituent selected from halo, lower alkyl, hydroxy, alkoxy and thioalkoxy; dialkylaminoalkyl; alkoxy; and thioalkoxy;

n is 1, 2 or 3;

$R_2$ is hydrogen or a lower alkyl;

$R_3$ is lower alkyl;

$R_4$ and $R_5$ are independently selected from phenyl, thiazolyl, and oxazolyl, wherein the phenyl, thiazolyl or oxazolyl ring is unsubstituted or substituted with a substituent selected from halo, lower alkyl, hydroxy, alkoxy, and thioalkoxy;

$R_6$ is hydrogen or lower alkyl;

$R_7$ is thiazolyl, oxazolyl, isoxazolyl or isothiazolyl, wherein the thiazolyl, oxazolyl, isoxazolyl or isothiazolyl ring is unsubstituted or substituted with lower alkyl;

X is hydrogen and Y is —OH, or X is —OH and Y is hydrogen, with the proviso that X is hydrogen and Y is —OH when Z is —N($R_8$)— and $R_7$ is unsubstituted, and with the proviso that X is hydrogen and Y is —OH when $R_3$ is methyl and $R_7$ is unsubstituted; and Z is absent, —O—, —S—, —CH$_2$— or —N($R_8$)— wherein $R_8$ is a lower alkyl, cycloalkyl, —OH or —NHR$_9$, wherein $R_9$ is hydrogen, lower alkyl or an N-protecting group; and a pharmaceutically acceptable acid addition, salt, ester, or prodrug thereof.

26. The method according to claim 16 wherein the HIV protease inhibitor or analog is a compound of the formula:

[structure]

wherein R is benzyloxycarbonyl or 2-quinolylcarbonyl; and a pharmaceutically acceptable acid addition, salt, ester, or prodrug thereof.

27. The method according to claim 16 wherein the HIV protease inhibitor is selected from the group consisting of nelfinavir, ritonavir, saquinavir, indinavir, amprenavir.

28. The method according to claim 27 wherein the HIV protease inhibitor is selected from the group consisting of ritonavir and saquinavir.

29. The method according to claim 28 wherein the HIV protease inhibitor is ritonavir.

30. The method according to claim 16 wherein the effective amount is less than a total amount required for chronic anti-retroviral suppression.

31. The method according to claim 16 wherein the effective amount is from about 300 mg to about 2400 mg.

32. The method according to claim 31 wherein the effective amount is from about 600 to about 1200 mg b.i.d.

33. The method according to claim 16 wherein the subject is provided with intermittent dosages separated by intervals of at least one week in which the drug is not administered.

34. The method according to claim 16 wherein the subject is provided with the HIV protease inhibitor or analog for a period of time less than or equal to about 72 hours.

35. The method according to claim 34 wherein the period of time is from about 6 to about 72 hours.

36. The method according to claim 34 wherein the period of time less than or equal to about 72 hours is subsequent to a cardiovascular ischemic event.

37. The method according to claim 36 wherein the cardiovascular ischemic event is induced by a thrombotic platelet aggregation or myocardial ischemia.

38. The method according to claim 37 wherein the myocardial ischemia is induced by myocardial infarction, angina, cardiac trauma, or arhythmia.

39. The method according to claim 37 wherein the thrombotic platelet aggregation induces a stroke.

40. The method according to claim 16 wherein the pharmaceutical composition comprises a pharmaceutically acceptable carrier, agent, counterion, adjuvant, or vehicle.

41. The method according to claim 16 wherein the HIV protease inhibitor or the analog is orally bioavailable.

42. The method according to claim 41 wherein the HIV protease inhibitor inhibits calpain about 20 times more effectively than PD150606, and wherein the inhibition constant for the HIV protease inhibitor is determined using supernatant extracted from PC12 cells, N-succinyl-leu-ter-7-amino-4-methylcoumarin as the substrate for calpain activity, with fluorescence measured with a 380 nm excitation filter and 480 nm emission filter, and inhibition determined using enzyme kinetic equations solved by nonlinear regression.

43. The method according to claim 16 wherein the pharmaceutical composition comprises another calpain inhibitor.

44. The method according to claim 16 wherein administering to the subject a therapeutically effective amount of a pharmaceutical composition comprises oral administration or administration by injection.

45. A method of inhibiting a calpain activity, comprising contacting a calpain with an effective amount of a calpain inhibitor selected from the group consisting of:

(1) a compound of the formula:

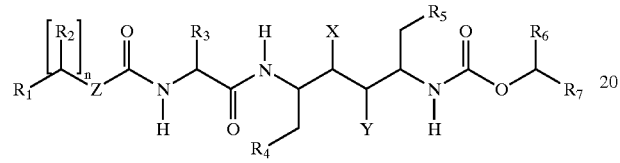

wherein $R_1$ is monosubstituted thiazolyl, monosubstituted oxazolyl, monosubstituted isoxazolyl, or monosubstituted isothiazolyl, and wherein the substituent is selected from: lower alkyl; lower alkenyl; cycloalkyl; cycloalkylalkyl; cycloalkenyl; cycloalkenylalkyl; heterocyclic, wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl; and wherein the heterocyclic is unsubstituted or substituted with a substituent selected from halo, lower alkyl, hydroxy, alkoxy and thioalkoxy; (heterocyclic)alkyl, wherein heterocyclic is defined as above; alkoxyalkyl; thioalkoxyalkyl; alkylamino; dialkylamino; phenyl, wherein the phenyl ring is unsubstituted or substituted with a substituent selected from halo, lower alkyl, hydroxy, alkoxy and thioalkoxy; phenylalkyl, wherein the phenyl ring is unsubstituted or substituted with a substituent selected from halo, lower alkyl, hydroxy, alkoxy and thioalkoxy; dialkylaminoalkyl; alkoxy; and thioalkoxy;

n is 1, 2 or 3;

$R_2$ is hydrogen or a lower alkyl;

$R_3$ is lower alkyl;

$R_4$ and $R_5$ are independently selected from phenyl, thiazolyl, and oxazolyl, wherein the phenyl, thiazolyl or oxazolyl ring is unsubstituted or substituted with a substituent selected from halo, lower alkyl, hydroxy, alkoxy, and thioalkoxy;

$R_6$ is hydrogen or lower alkyl;

$R_7$ is thiazolyl, oxazolyl, isoxazolyl or isothiazolyl, wherein the thiazolyl, oxazolyl, isoxazolyl or isothiazolyl ring is unsubstituted or substituted with lower alkyl;

X is hydrogen and Y is —OH, or X is —OH and Y is hydrogen, with the proviso that X is hydrogen and Y is —OH when Z is —N($R_8$)— and $R_7$ is unsubstituted, and with the proviso that X is hydrogen and Y is —OH when $R_3$ is methyl and $R_7$ is unsubstituted; and Z is absent, —O—, —S—, —$CH_2$— or —N($R_8$)— wherein $R_8$ is a lower alkyl, cycloalkyl, —OH or —$NHR_9$, wherein $R_9$ is hydrogen, lower alkyl or an N-protecting group;

(2) a compound of the formula:

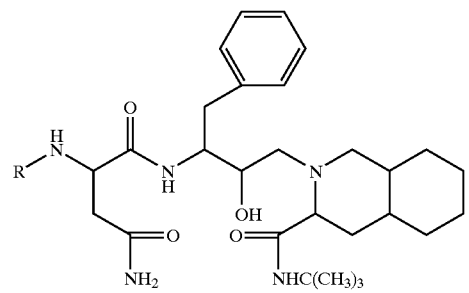

wherein R is benzyloxycarbonyl or 2-quinolylcarbonyl;

(3) indinavir;

(4) nelfinavir;

(5) amprenavir; or (6) a combination of any of (1)–(5); and a pharmaceutically acceptable acid addition, salt, ester, or prodrug thereof.

46. The method according to claim 45 wherein the calpain inhibitor is selected from the group consisting of ritonavir, saquinavir, indinavir, nelfinavir, amprenavir.

47. The method according to claim 46 wherein the calpain inhibitor is ritonavir or saquinavir.

48. The method according to claim 45 wherein the method of inhibiting a calpain comprises a method of treating a condition mediated by calpain.

* * * * *

UNITED STATES PATENT AND TRADEMARK OFFICE
CERTIFICATE OF CORRECTION

PATENT NO. : 6,448,245 B1
DATED : September 10, 2002
INVENTOR(S) : DePetrillo et al.

It is certified that error appears in the above-identified patent and that said Letters Patent is hereby corrected as shown below:

Column 8,
Line 53, "cornmonly" should read -- commonly --.

Column 16,
Line 57, "experime ntal" should read -- experimental --.
Line 64, "centrifulgation" should read -- centrifugation --.

Column 17,
Line 2, "14,000 g" should read -- 14,000g --.

Column 18,
Line 9, "$\leqq$" should read -- $\leq$ --.

Column 19,
Line 39, "MEM+was" should read -- MEM+ was --.

Column 25,
Line 19, "valinyl" should read -- alaninyl --.
Line 34, "(2S, 3R" should read -- 2S, 3R --.
Line 44, "amino" should be deleted.

Column 27,
Line 6, "valinyl" should read -- alaninyl --.

Signed and Sealed this

Nineteenth Day of August, 2003

JAMES E. ROGAN
*Director of the United States Patent and Trademark Office*